United States Patent [19]

Turner

[11] Patent Number: 4,462,412
[45] Date of Patent: Jul. 31, 1984

[54] ANNULAR ELECTROMAGNETIC RADIATION APPLICATOR FOR BIOLOGICAL TISSUE, AND METHOD

[75] Inventor: Paul F. Turner, North Salt Lake, Utah

[73] Assignee: BSD Medical Corporation, Salt Lake City, Utah

[21] Appl. No.: 136,506

[22] Filed: Apr. 2, 1980

[51] Int. Cl.$^3$ ............................................. A61N 1/40
[52] U.S. Cl. .................................................... 128/804
[58] Field of Search ................................. 128/1.3–1.5, 128/783, 798, 804, 420 A; 219/10.79

[56] References Cited

U.S. PATENT DOCUMENTS

| | | | |
|---|---|---|---|
| 3,077,195 | 2/1963 | Fulsche | 128/804 |
| 3,800,802 | 4/1974 | Berry et al. | 128/804 X |
| 3,895,639 | 7/1975 | Rodler | 128/420 A |
| 4,140,130 | 2/1979 | Storm | 128/804 X |
| 4,186,729 | 2/1980 | Harrison | 128/804 X |
| 4,271,848 | 6/1981 | Turner et al. | 128/804 |
| 4,282,887 | 8/1981 | Sterzen | 128/804 |

FOREIGN PATENT DOCUMENTS

| | | | |
|---|---|---|---|
| 1135587 | 8/1962 | Fed. Rep. of Germany | 128/804 |
| 2364970 | 7/1975 | Fed. Rep. of Germany | 128/804 |
| 2420883 | 11/1975 | Fed. Rep. of Germany | 128/804 |

Primary Examiner—Lee S. Cohen
Attorney, Agent, or Firm—Hubbard, Thurman, Turner & Tucker

[57] ABSTRACT

A method is described for selecting an electromagnetic radiation (EMR) frequency causing substantially uniform heating in cylindrical biological tissue specimens, having a typical cross-sectional dimension, d, and known electrical properties, by an annular applicator configured for applicator-specimen impedence matching. Accordingly, an annular applicator system (10) comprises an EMR source (32) having a selected frequency wavelength in a specimen (20) between two-thirds and twice the specimen dimension, d. Connected to the source (32) is an annular applicator apparatus (12) formed of four applicator segments (16), circumferentially arranged to form an axial specimen receiving opening (18). A composite EMR emitting aperture (22), formed around the opening (18) has an axial height to circumferential width ratio causing matching, at the selected frequency, between a characteristic impedance of the apparatus (12) and a load impedance of the specimen (20) as seen through the aperture. A line splitter (36) enables parallel EMR connection of the segments (16) to the source (32). Two variation annular apparatus (200) and (252) are described.

15 Claims, 15 Drawing Figures ns
ANNULAR ELECTROMAGNETIC RADIATION APPLICATOR FOR BIOLOGICAL TISSUE, AND METHOD

TECHNICAL FIELD

The present invention relates generally to the field of apparatus for irradiating biological tissue with electromagnetic radiation for medical hyperthermia purposes, and more particularly to annular-type radiation applicators associated with such hyperthermia apparatus.

BACKGROUND ART

Several types of therapeutic treatments for cancer in humans are in current, common use. These treatments include surgery, x-rays or radiation from radioactive sources and chemotherapy, these treatments being often combined in various ways to enhance treatment effectiveness.

Although such conventional treatment techniques have been successful in treating cancer in many patients and in prolonging the lives of many other patients, they are not only frequently ineffective against many types of cancer, but very often, if not usually, have severely adverse side effects at the necessary treatment levels. Protracted treatment of cancer patients by x-rays or chemotherapy, as an illustration, tends to eventually destroy or inhibit the patients' natural immunological systems to an extent that many patients eventually succumb to common infectuous diseases, such as influenza or pneumonia, which otherwise probably would not be fatal. Also, many patients having advanced stages of cancer or complications may become too weak to withstand the trauma of surgical or other cancer treatments; hence, the treatments cannot be undertaken or must be discontinued.

Due both to the prevalence and the typically severe consequences of human cancer, as well as frequent ineffectiveness of current treatments such as those mentioned above, medical researchers are continually experimenting to attempt to discover and develop improved or alternative cancer treatment methods with their associated treatment apparatus.

For centuries, hyperthermia, that is, artificially elevated body temperature, has been known to be quite effective in treating many types of bodily disorders, duplicating, in effect, the body's own fever defense mechanism. More recently, hyperthermia has become an important area of research into its possible use and effectiveness, either alone or in combination with more conventional cancer treatments, in treating cancer in humans. This research is important in that hyperthermia techniques appear to have the potential of being extremely effective for treating many or most types of human cancers, without the often severely adverse side effects associated with current cancer treatments.

Researchers into hyperthermia treatment of cancer have commonly reported that many types of malignant growths in humans can be thermally destroyed, usually with no seriously adverse side effects, by heating the malignancies to temperatures slightly below that injurious to most normal, healthy cells. Furthermore, many types of malignant cell masses have reportedly been found to have substantially poorer than normal heat transfer or dissipation characteristics, presumably due to poorer vascularity and reduced blood flow characteristics. Consequently, these types of growths appear capable of preferential hyperthermia treatment. Poorly vascular malignant growths, as a result, can reportedly be heated to temperatures several degrees higher than that which immediate surrounding healthy tissue reaches. This promises to enable hyperthermic treatment of those types of malignant growths which are no more thermally sensitive than normal tissue without destruction of normal cells, and additionally to enable higher temperature, shorter hyperthermia treatment times of more thermally sensitive types of malignancies which exhibit poor vascularity, usually an advantage for important medical reasons.

In this regard, researchers have commonly reported that as a consequence of these thermal characteristics of most malignant growths and the thermal sensitivity of normal body cells, hyperthermia temperatures for treatment of human cancer should be carefully limited within a relatively narrow effective and safe temperature range. Below a threshold temperature of about 41.5° C. (106.7° F.), significant thermal destruction of most malignant growths of cells has normally not been found to occur. At lower hyperthermic temperatures, undesirable growth of many types of malignancies, to the contrary, is believed to be stimulated.

At slightly higher hyperthermic temperatures, in or above the approximate range of 43° C. to 45° C. (109.4° F. to 113° F.), thermal damage to most types of normal cells is routinely observed; thus, great care must be taken not to exceed these temperatures in healthy tissue. Exposure duration at any elevated temperature is, of course, an important factor in establishing extent of thermal damage to healthy tissue. However, if large or critical regions of the human body are heated into, or above the 43° C. to 45° C. range, for even relatively short times, serious permanent injury or death may be expected to result. As an example, in a book entitled "Recent Results in Cancer Research, Selective Heat Sensitivity of Cancer Cells", edited by A. Rossi-Fanelli et al, published by Springer-Verlug; Berlin, Heidelberg, New York, 1977, experimental observations on thermal sensitivity of malignant growths and cells are discussed, observed thermal death times being characterized as a straight line on a time vs temperature, semi-logarithm plot (at Page 97).

Various common types of skin or near surface cancers in humans have frequently been found to respond favorably to treatment by direct application of surface heat, for example, by hot fluid baths which cause surface hyperthermia at the applied region. However, more deeply located malignant growths, principally due to characteristic blood flow heat transferring properties of intervening healthy tissue, cannot reliably be heated to a destructive temperature by surface heating, without probability of causing, at the same time, excessive damage to the overlying healthy tissue.

A non-surface heating technique involving artifically inducing a high body fever in the patient by exposure to a contageous disease, has sometimes in the past been used, but has seldom been satisfactory because of the difficulty in maintaining the fever in the permissible hyperthermia treatment range and the danger to the patient, from the disease itself, when the fever is permitted to remain at necessary high temperature levels. Alternatively, whole body heated blood perfusion hyperthermia techniques have also generally been unsatisfactory, due to the slowness of the treatment and trauma to the patient.

Because of these and other deficiencies in pre-existing hyperthermia techniques for treating cancer in humans, possibility of using highly penetrating electromagnetic radiation (EMR) to induce biological hyperthermia in living tissue is currently under serious investigation as an attractive alternative, particularly for hyperthermic treatment of deeply located and/or widely metasticized malignant growths, but also for surface or near-surface malignancies.

Historically, alternating electric currents, at frequencies above about 10 KHz, were found late in the last century to penetrate and cause heating in biological tissue. As a result, high frequency electric currents, usually in the megahertz frequency range, have since been widely used for therapeutic treatment of such common bodily disorders as infected tissue and muscle injuries. Early in this century, the name "diathermia" was given to this EMR tissue heating technique, and several discrete EMR frequencies in the megahertz range have subsequently been allocated spedifically for diathermy use in this country by the Federal Administration Commission (FCC).

Experimental therapeutic treatment of malignant growths in living tissue by high frequency EMR induced hyperthermia has been reported at least as early as 1933. For example, in an article by Dr. J. W. Schereschewsky entitled "Biological Effects of Very High Frequency Electromagnetic Radiation", published in *RADIOLOGY*, April, 1933, curative or inhibitory effects of EMR hyperthermia on mice tumors, at EMR frequencies up to 400 MHz, was described. A summary of research in the EMR hyperthermia field was also presented by Schereschewsky. More recently, for example, researchers Guy, Lehman and Stonebridge in 1974 summarized the background of high frequency EMR medical hyperthermia research and discussed then current experimental activity in the field, in their article entitled "Therapeutic Application of Electromagnetic Power", appearing in the *PROCEEDINGS OF THE IEEE*, Volume 62, No. 1, in January, 1974.

A number of even more current discussions relating to EMR hyperthermia treatment of cancer may, for example, be found in a compilation of articles on the subject published in the book "Cancer Therapy by Hyperthermia and Radiation", edited by Christian Streffer et al and published by Urban and Schwarzenberg; Baltimore, Munich 1978.

In spite of there having been reported encouraging and often apparently successful medical results obtained by using EMR induced hyperthermia to treat malignant growths in humans, the treatments have normally been of an experimental nature, typically being used on cancer patients otherwise considered incurable or terminal, since serious problems relating to hyperthermic damage to healthy tissue have commonly been encountered. As with conventional surface heating, these healthy tissue damage problems are particularly associated with thermally destroying malignant growths deeply located in, or close to, thermally sensitive tissue.

This unintended EMR thermal damage of healthy tissue can typically be attributed to design and use of existing EMR irradiating apparatus, rather than to any basic deficiency in the concept of EMR hyperthermia treatment. EMR apparatus used, for example, often radiate excessive and/or improperly controlled EMR heating fields. A further disadvantage is that the specific diathermy allocated frequencies which are ordinarily used are typically non-optimum radiating frequencies for deep penetration. In addition, existing EMR hyperthermia apparatus and techniques tend to increase incidence and severity of thermal "hot spotting" in healthy tissue, as may be caused by constructive interference of applied energy waves, either by characteristic reflections at interfaces between different types of tissue, or by simultaneous use of more than one EMR applicator.

To overcome these and other problems associated with heretofore available EMR hyperthermia apparatus used for medical research or other medical purposes, applicant has disclosed improved EMR hyperthermia apparatus in U.S. patent applications, Ser. No. 002,584, now U.S. Pat. No. 4,271,848, and Ser. No. 048,515, now U.S. Pat. No. 4,341,227, filed on Jan. 11, 1979 and June 14, 1979, respectively. In these two patent applications, parallel plate and waveguide-type EMR applicators, together with associated EMR systems, were described and claimed, the applicators being particularly adapted for irradiating biological tissue or tissue simulating matter from outside the tissue. Emphasis was placed on broad band EMR capabilities, enabling, for example, research definition of important parameters associated with hyperthermic treatment of malignancies in humans. Also described in such patent applications was simultaneous operation of two (or more) applicators arranged to improve deep tissue heating characteristics.

In applicant's subsequent U.S. patent application, Ser. No. 050,050, filed on June 19, 1979, now abandoned needle-type, invasive EMR applicators, for enabling EMR hyperthermia in sub-surface tissue regions, were described. By surrounding, with a phased array of these invasive applicators, a localized tissue region, such as a region containing a malignant growth, substantially uniform heating of the surrounded region by constructive interferences of the sychronous EMR fields was described.

However, there still exists an important need for EMR hyperthermia apparatus capable of causing uniform deep EMR heating of thick tissue masses, such as trunk and thigh portions of an adult human body, in which large or widely dispersed malignant growths may be found. For these and similar regions of the body, an encircling annular EMR applicator apparatus, which may comprise an array of smaller applicators, is ordinarily prefered so that EMR energy is emitted inwardly from all around the enclosed body region to be EMR heated.

To this end, large annular magnetic coils have been used to radiate a magnetic field into a body region disposed through the coil. Although such radiated magnetic fields are known to penetrate deeply in human tissue, uniform heating across the encircled tissue region is still difficult to achieve. This is because a decreasingly smaller volume of tissue is presented for magnetic field coupling as the center of the encircled tissue region is approached. Thus, when such annular magnetic coils are used to cause hyperthermia in biological tissue, surface tissue regions can be expected to be heated much more than underlying central tissue regions.

Similar thermal gradients appear to result from heretofore available annular EMR applicators, which have typically been constructed from a number of individual applicators of types used for local EMR heating. Although some improvements in deeper heating can ordinarily be expected from positioning, and operating in unison, a number of individual EMR applicators around a tissue region, the necessary uniformity of tissue heating can ordinarily only be expected with heretofore ignored specific design consideration relating to tissue characteristics and radiating aperture configuration.

Considering the above cited narrow, effective and safe thermal treatment range of only about 4° C., necessity for a low thermal gradient across the encircled tissue can be seen as necessary if all types of malignant growths are to be capable of successful treatment by hyperthermia techniques. Consequently, uniformity of specimen heating should be a very important design objective of EMR apparatus.

When, however, success in thermally treating deeply located malignant growths by heretofore available types of annular applicator apparatus have been experienced, the results appear to be more attributable to poorer heat dissipation properties of large malignant growths than to the desirable uniformity of heating. Heating uniformity, not heretofore available, would also enable effective thermal treatment, for example, of deeply located, widely dispersed, small groups of malignant cells in early stages of growth before the associated reduced heat transfer characteristics become significant. Ability to provide at least substantially uniform heating of encircled tissue regions is also very important, for example, in areas of EMR hyperthermia research into hyperthermic effects on normal healthy tissue.

In addition to the difficult medical related problems associated with non-uniform EMR tissue heating, heretofore available annular applicators typically have other problems. As an example, because of poor impedance matching with the tissue region being irradiated, most available apparatus are narrow band apparatus and usually require power from the source to be much greater than that actually radiated into the tissue specimen. This requires the apparatus to be substantially more expensive than would otherwise be necessary, not only because of the usually much greater cost of a higher power EMR source, but also because of specially required tuning devices and high temperature resistant components in which the lost power is converted to heat. Also the amount of stray radiation leakage also tends to be increased, such impedance mismatched EMR apparatus thereby requiring expensive EMR shielding to prevent possible radiation danger for operators of the apparatus.

For these and other reasons, applicant has invented annular EMR applicator apparatus, and corresponding methods for EMR irradiation, which provide greatly improved uniformity of EMR heating in an encircled region of biological tissue or tissue simulating matter. Applicant's improved annular applicator apparatus provides such heating uniformity for whatever purposes the EMR heating may be required or desired, whether or not these purposes relate to medical hyperthermic treatment of cancer or of other bodily disorders and diseases or to other areas of medical research.

DISCLOSURE OF INVENTION

In accordance with the present invention, an electromagnetic radiation hyperthermia system, for causing substantially uniform electromagnetic radiation (EMR) heating in generally cylindrical biological tissue specimens having a preestablished typical cross-sectional dimension and known lossy material electrical properties, comprises a source of electromagnetic radiation energy at a preselectable radiation frequency, f, and an annular applicator apparatus. Such applicator apparatus has a specific characteristic impedance and includes radiation input portions and means defining a central, axial opening sized to receive the tissue specimens for EMR irradiation thereof. The central opening defining means also defines a peripheral radiation emitting aperture around and along the opening, the aperture having an axial height, h, and circumferential length, w, selected for causing impedance matching, at the selected frequency, f, between the applicator apparatus characteristic impedance and a load impedance of received specimens as presented to the emitting aperture. Such impedance matching not only adds to uniformity of specimen EMR heating, but also enables relatively broad band operation to accommodate typical variations in specimen size and type. Also included in the system are electromagnetic radiation transmission means for interconnecting the source with the radiation input portions of the applicator apparatus.

More particularly, the source radiation frequency, f, is preselected to cause, in specimens received in the applicator apparatus opening, a corresponding wavelength to be a preselected function of the specimen typical cross-sectional dimension. The radiation frequency, f, is preferably selected to cause the corresponding wavelength in the received specimens to be between two-thirds and twice the specimen typical cross-sectional dimension, so as to provide additive wave interference, and hence energy and heating enhancement, in specimen central regions.

EMR coupling between the emitting aperture and received specimens, is enhanced by including in the applicator apparatus a flexible, annular, fluid containing envelope disposed around the central opening, in space filling relationship between the applicator apparatus and specimens received thereinto.

The applicator apparatus may be constructed in composite form from an electrically parallel, array of applicator segments, each segment having the same characteristic impedance. Thus the applicator apparatus characteristic impedance is a parallel sum of the applicator characteristic impedances. Segment characteristic impedances are preferably selected to be 50 ohms so as to be comparable with 50 ohm impedances of conventional EMR components.

Included in the EMR transmission between the source and the applicator apparatus means is a line splitter, a 50 ohm first transmission line connected between the source and the line splitter and a plurality of 50 ohm second transmission lines connected in parallel between the line splitter and radiation input portions of the applicator segments, the line splitter enabling sychronous operation of all the applicator segments from the common source.

Dielectric loading of the segments is provided by dielectric fluid filling at least radiation emitting regions of the applicator segments. To enable surface region cooling of specimens being irradiated, as may sometimes be necessary or desirable to enhance specimen heating uniformity, means are included for flowing the dielectric fluid through segment radiation emitting regions. To enable use of distilled water as the dielectric fluid, while avoiding substantial emitted field discontinuities, applicator regions of the segments include a plurality of spaced apart, radial strips of dielectric material.

In a particular configuration, the applicator apparatus includes four 90° segments, each comprising a two-by-two array of individual EMR applicators.

In one variation, a coaxial applicator apparatus comprises a single applicator having a closed, electromagnetic radiation input end and an open, specimen receiving end. Such applicator includes inner and outer electrically conductive shells arranged in spaced apart, coaxial relationship, each of the shells including a radially diverging region at the input end and a radially converging region at an opposite end. The radial converging end regions of the shells are axially spaced apart, with the converging end region of the outer shell more remote from the input end than the converging end region of the inner shell, a radiation emitting aperture being defined between the converging end regions. The outer conductive shells are formed having a generally cylindrical, intermediate region between the diverging and converging end regions thereof. Both the inner and outer shells are circular in cross section at any transverse cross section and are spaced apart, in all regions, distances providing a substantially uniform impedance along the applicator.

Individually, the applicator apparatus can be used in other types of EMR irradiating biological tissue specimens. However, the advantages associated with the apparatus are particularly achieved in systems adapted for causing electromagnetic radiation heating in generally cylindrical biological tissue specimens having a preselected typical cross-sectional dimension and known lossy material electrical properties, the systems including a source of electromagnetic radiation energy and electromagnetic energy transmission means connected to the source for transmission of electromagnetic energy therefrom to the applicator apparatus.

A corresponding method for electromagnetic radiation heating of a generally cylindrical, biological tissue specimen, comprises the steps of determining a typical cross-sectional dimension and lossy material properties of typical specimens to be irradiated and selecting, from the specimen typical cross-sectional dimension and lossy material properties, a electromagnetic radiation heating frequency for causing specimen deep heating. Included are the steps of determining from the selected electromagnetic radiation frequency and specimen lossy material properties, a typical specimen dielectric constant and determining from the typical specimen dielectric constant, size of a radiation emitting aperture of an annular radiation applicator apparatus which provides, at the selected frequency, impedance matching between a characteristic impedance of the applicator apparatus and a load impedance of the typical specimens as seen through the aperture and constructing an annular applicator apparatus in accordance therewith. After receiving the typical specimens into the annular applicator apparatus, the specimens are irradiated at the selected electromagnetic radiation frequency.

Included in the step of selecting a radiation frequency is the step of determining an electromagnetic wavelength in the typical specimens which is between two-thirds and twice the specimen typical cross-sectional dimension. The step of determining the size of the radiation emitting aperture includes the step of establishing a preferred load, impedance of the specimens based upon a characteristic impedance of the applicator and constructing the emitting aperture having a height-to-length ratio enabling the specimen impedance, as seen through the aperture, to equal the preferred load impedance.

Further, the step of constructing an annular applicator apparatus includes constructing the apparatus from a preselected parallel arrangement of a plurality of applicator segments each having a predetermined characteristic impedance, the characteristic impedance of the applicator apparatus being the parallel sum of the individual segment impedances, the segments each being connected in electrical parallel to a common electromagnetic energy source, thereby enabling sychronous operation of the segments. The method may include the step of varying the electromagnetic radiation energy phase to selected ones of the applicator segments in a manner enabling shifting of a tissue heating pattern in the specimens. Alternatively, the step of constructing an annular applicator includes forming a single 360° coaxial applicator having a single EMR radiating aperture.

BRIEF DESCRIPTION OF THE DRAWINGS

A better understanding of the present invention may be had from a consideration of the following detailed description, taken in conjunction with the accompanying drawings in which.

BEST MODE OF CARRYING OUT INVENTION

Figure 1:
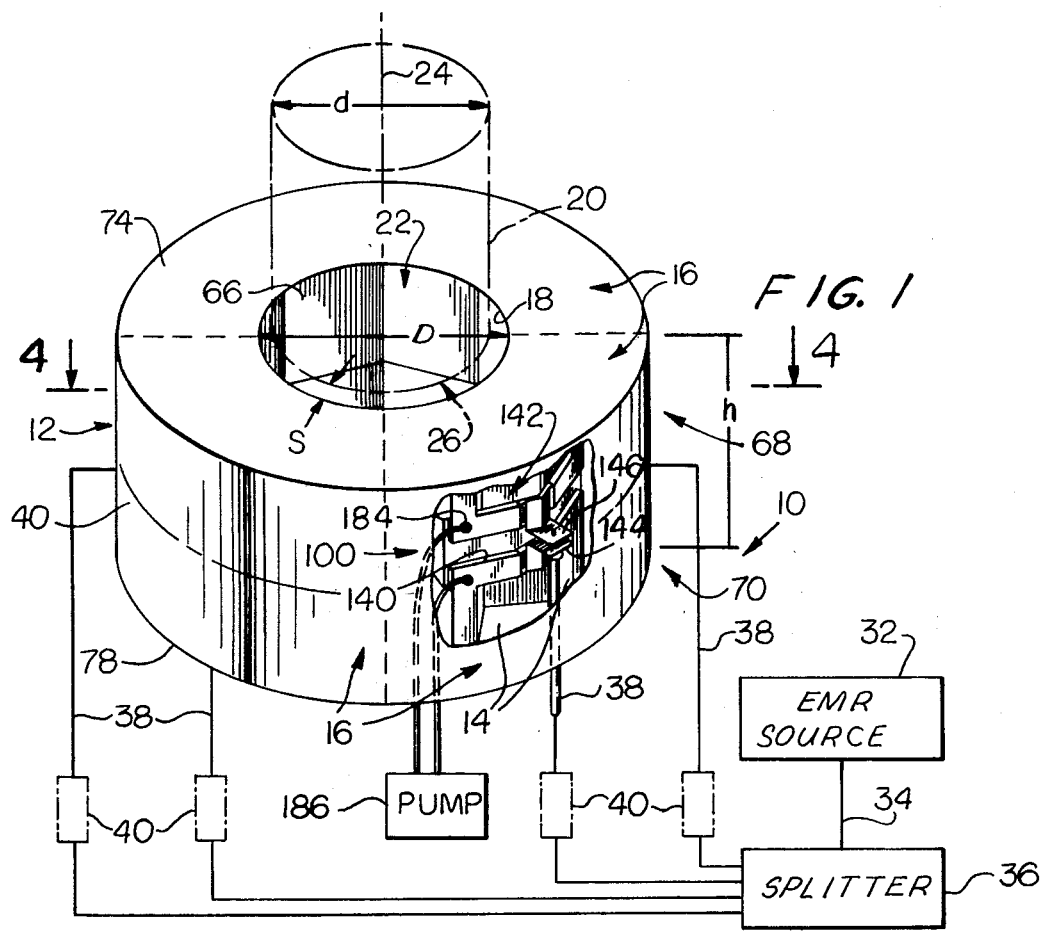
FIG. 1 is a partially cut away and partially schematic perspective drawing of an electromagnetic radiation (EMR) heating system having an annular applicator apparatus for EMR heating of generally cylindrical biological tissue specimens.

As shown generally in FIG. 1, an exemplary electromagnetic radiation (EMR) hyperthermia system 10, according to the present invention, comprises an annular applicator apparatus 12 constructed for EMR irradiation and uniform EMR heating of biological tissue. The term "biological tissue" as used herein is to be construed broadly to include not only actual biological tissue but also materials simulating biological tissue, such as "phantom tissue", of types commonly used for experimental EMR hyperthermia purposes. As shown, and as more particularly described below, the applicator apparatus 12 comprises an integrated array of individual or discrete EMR applicators 14 which are formed into a plurality of applicator apparatus segments 16.

Formed axially through the applicator apparatus 12 is a cylindrical opening 18 configured to receive therethrough a generally cylindrical biological tissue specimen 20, such as regions of a human limb or trunk, size of the opening generally depending upon size of the specimen, as described below. Defining an outer periphery of the applicator opening 18 is a circumferential radiation aperture or window 22 through which electromagnetic radiation from the apparatus 12 is emitted radially inwardly towards the specimen 20, and hence towards a longitudinal applicator axis 24.

A diameter, D, of the opening 18 and height, h, of the applicator apparatus 12 are equal, also as described below, to dimensions of the radiation emitting aperture 22. To enable good EMR coupling into the specimen 20, a spacing or gap of width, S, between the radiation aperture 22 and the specimen 20 is preferably completely filled by a water filled bolus or flexible annular envelope 26. A more uniform emitted EMR field is assured by establishing the gap width, S, at several centimeters.

Further comprising the system 10 is an electromagnetic radiation source or generator 32. To an EMR output of the source 32 is connected a first EMR transmission line or means 34, which perferably comprises a conventional 50 ohm impedance coaxial cable.

Connected to a remote end of the transmission line 34, for the exemplary plural segmented applicator apparatus 12 of FIG. 1, is a conventional parallel coaxial line splitter 36. A plurality of equal length second EMR transmission lines or means 38 interconnect the line splitter 36 with each of the applicator segments 16 for sychronous applicator operation. For the illustrative four segmented apparatus 12, four parallel transmission lines 38, each preferably comprising a conventional 50 ohm coaxial cable, are used.

Non-sychronous EMR phase variation or shifting between the plurality of lines 38, as may sometimes be necessary or desirable to shift the EMR heating pattern in the specimen 20, as described below, may be enabled by including in series in each of such lines a conventional "line stretcher" 40, by means of which the EMR length of the lines may be selectively varied.

Greatly improved uniformity of EMR heating in the irradiated tissue specimen 20 is achieved by carefully considering important relationships between the EMR irradiating frequency, f, and applicator configuration, for example, height, h, and diameter. D, of the applicator apparatus aperture 22, relative to a diameter, d, (or other typical cross sectional dimension) and composition of the specimen.

As is well known, electromagnetic wave amplitude is attenuated as the corresponding wave propagates into any lossy medium; the more lossy the medium, the greater the wave attenuation. EMR power density, being related to EMR wave amplitude, is thus also attenuated as depth of wave penetration increases, such power loss or attenuation being commonly expressed in terms of decibels per centimeter of material (db/cm). Furthermore, since EMR heating is, in turn, a function of EMR power density, the EMR heating effect is similarly reduced or attenuated as depth of wave penetration into a lossy medium increases.

Extent of electromagnetic wave amplitude and power density attenuation with depth of EMR wave penetration into a lossy medium is also commonly known to be dependent upon applied EMR frequency, f, as well as upon electrical properties of the medium into which the waves are propagated. Although the human body varies considerably in composition, most regions of the body, for purposes of the ensuing discussion, can be considered as comprised of one of two general types of EMR lossy material: a high lossy type (H-type), typified by muscle, skin and high water content tissue; and a low lossy type (L-type), typified by fat, bone and low water content tissue.

EMR power density attenuation or loss factors (in db/cm) for each of these general H- and L-type body compositions can be experimentally determined as a function of applied EMR frequency, and typical values are presented in Table 1, "LOSS H" being the EMR power density loss factor in typical H-type material and "LOSS L" being the corresponding loss factor in typical L-type material. From Table 1, the power density loss factors, Loss H and Loss L, are seen to increase with applied frequency, f; at any given frequency Loss H is much higher than Loss L, as should be expected. The data presented in Table 1 corresponds generally to that reported, for example, by Curtis Johnson and Arthur Guy in their article entitled "Ionizing Effects in Materials and Systems", which appears in the PROCEEDINGS OF THE IEEE, Volume 60, No. 6, June, 1972 (page 692 et seq.).

TABLE 1

| | Plane Wave Properties of Tissue | | | |
|---|---|---|---|---|
| Applied Frequency f. MHz | Hi-Water Content Loss H (db/cm) | Low Water Content Loss L (db/cm) | Hi-Water Content $\lambda H$ (cm) | Low Water Content $\lambda L$ (cm) |
| 27.12* | 0.61 | 0.055 | 68.1 | 241 |
| 40.68 | 0.78 | 0.074 | 51.3 | 187 |
| 100 | 1.304 | 0.144 | 27 | 106 |
| 200 | 1.81 | 0.222 | 16.6 | 59.7 |
| 300 | 2.23 | 0.271 | 11.9 | 41 |
| 433 | 2.43 | 0.332 | 8.76 | 28.8 |
| 750 | 2.73 | 0.378 | 5.34 | 16.8 |
| 915* | 2.86 | 0.491 | 4.46 | 13.7 |

*FCC approved diathermy frequencies

From these loss factors, Loss H and Loss L, of Table 1, "penetration depths" or depth in centimeters, which an electromagnetic wave in a propagating medium travels before its power density decreases by a conventional factor of $e^{-2}$, or 8.69 db, can readily be defined. Beyond these penetration depths, only negligible EMR tissue heating can be expected to occur.

It should be apparent from Table 1 that an optimum applied EMR heating frequency, f, can be selected, for a particular type of material to be irradiated, according to required depth of EMR energy density penetration, as determined by the corresponding Loss H or Loss L factors. Table 1 shows, for example, that the greater the depth of penetration and heating required, the lower should be the applied EMR frequency, f. Thus, the higher megahertz frequencies have relatively poor penetration characteristics and cannot be expected to cause deep tissue heating without excessive heating of surface regions. Substantial depths of energy penetration at higher frequencies can only be achieved by deposition of excessive electromagnetic power densities at the specimen surface.

EMR wave length corresponding to the applied EMR frequency, f, is also commonly known to depend upon the type of material in which the electromagnetic wave is propagated. Accordingly, Table 1 also lists experimentally determined wave lengths corresponding to each of the listed frequencies, $\lambda H$ being the wave length in H-type material and $\lambda L$ being the wave length in L-type material. From Table 1 it can be seen, for example, that for any given applied frequency, f, the corresponding wave length, $\lambda H$, is several times shorter than that of the corresponding wave length, $\lambda L$.

As an illustration, Table 1 lists, for an applied frequency, f, of 200 Mhz, a power density loss, Loss H, in H-type material of 1.81 db/cm and a corresponding wave length, $\lambda H$, of about 16.6 centimeters (6.54 inches). At the same frequency, in L-type material the power density loss, Loss L, is seen to be only 0.222 db/cm with the corresponding wave length, L, being 59.7 centimeters (23.5 inches). Practical effects of wave length variation with frequency and specimen type will become more significant from the ensuing discussion.

Because of this characteristic power density attenuation as electromagnetic waves propagate into a lossy medium, the power density and corresponding tissue heating, when the specimen is irradiated by plane EMR waves from a single direction, is usually substantially less in specimen central regions than near specimen surface regions, unless the specimen is quite small in diameter or cross sectional size. Thus, assuming for further illustrative purposes that an irradiated H-type specimen is 15 centimeters (5.9 inches) in diameter, which corresponds to a typical leg diameter, a central region power density, $P_{C1}$, normalized to surface power density, $P_S$, is given by the following expression:

$$P_{C1} = 7.5 \text{ cm} \times \text{Loss H} \tag{1}$$

For example, at the mentioned applied frequency, f, of 200 Mhz, central region power density, $P_{C1}$, in the 15 cm diameter specimen is about 13.6 db less than the surface power density, or only about 4.4 percent thereof. Thus, a substantial thermal gradient would normally occur across the specimen, with the central region being much cooler than surface regions. Deep tissue heating, for whatever purpose that might be desired, cannot, therefore, be expected in this example to be achieved by irradiation from a single direction without causing excessive tissue surface region heating.

When any lossy medium, such as a specimen 50, (FIG. 2a), is, however, irradiated from opposite directions onto sides 52 and 54 by identically polarized waves, regions of constructive (additive) and regions of destructive (subtractive) wave interference from the two waves are expected to occur within the specimen. For simplicity of analysis, the specimen 50 is shown in FIGS. 2a and 2b to have a square cross section. Within the specimen 50, in regions of overlapping additive wave interference, the power density, and hence the resulting tissue heating, is greater than elsewhere in the specimen. In contrast, in specimen regions of overlapping but subtractive interference, the power density, and hence tissue heating, is less than elsewhere in the specimen. Irradiation of the specimen from the opposite sides 52 and 54 can thus be expected to cause localized higher and lower temperature regions in the specimen.

These additive wave interference effects can be utilized to enhance specimen central region heating, thereby improving uniformity of heating across the specimen 50. When the specimen 50 is irradiated from the opposite sides 52 and 54 by EMR waves of appropriate matching frequencies, phase polarization and power, a standing wave is established in the specimen due to the overlapping synchronous electric field. If polarization of the two EMR waves is alligned, as indicated, parallel to the sides 52 and 54 and into the plane of FIGS. 2a and 2b a synergistic additive wave effect is achieved in the specimen central region. Under these particular conditions, the electric fields from the two EMR waves add directly, in regions of constructive wave interference, to cause a four-fold power density increase in central specimen regions, due to the known squared relationship between electric field strength and power density. A central region power density, $P_{C2}$, due to simultaneous EMR irradiation from the opposite directions shown is thus given by the expression:

$$P_{C2} = 4P_{C1} \tag{2}$$

However, if polarization of the two irradiating electromagnetic waves were, instead, perpendicular, the total central power density would be only the sum of the two individual central region power densities, much less specimen central region heating thereby occuring.

As is shown by FIG. 2b, two additional independent directions exist from which the specimen 50 can be irradiated by sychronous, electromagnetic waves having polarization matching the previously discussed two waves. With these two additional electromagnetic waves directed at remaining opposite sides 56 and 58 of the specimen 50, the electric field in central regions of the specimen will be four times that of a single electromagnetic wave. Hence, a corresponding central power density, $P_{C4}$, is given by the equation:

$$P_{C4} = 16P_{C1} \tag{3}$$

If the electromagnetic frequency, f, is properly selected, as discussed below, so that the combined additive field effects on the specimen surface power density, $P_S$, from the four waves is negligibly small, the central power density, $P_{C4}$, resulting from the four waves, for the described example in which $P_{C1} = 4.4\% \ P_S$, is $16 \times 4.4\%$ or 70.4% of the surface power density $P_S$. Central region EMR heating, under these circumstances, will correspondingly be approximately 70% of that caused in specimen surface regions. With such a level of central region heating, sufficient specimen surface cooling can ordinarily be provided, for example, by water cooling, to enable substantially uniform specimen heating.

Figure 2C:
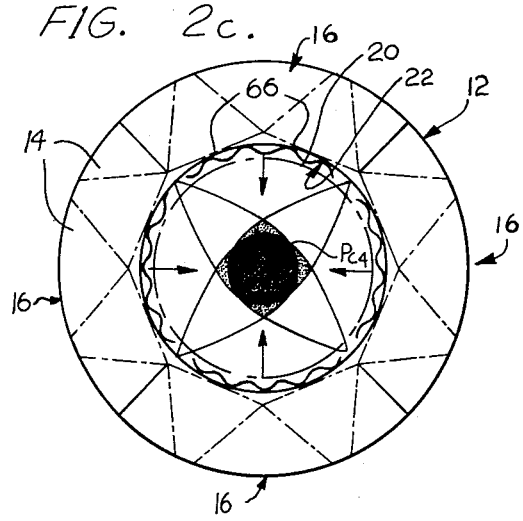
FIG. 2 is a diagramatic representation illustrating effects of EMR irradiating a cylindrical tissue specimen from a plurality of independent directions.
FIG. 2a illustrating effects of EMR irradiating an idealized square cross section specimen from two opposite sides, FIG. 2b illustrating effects of EMR irradiating the square cross section specimen from four different sides, and FIG. 2c illustrating effects of EMR irradiating a circular cross section specimen by an annular applicator similar to that of FIG. 1.
Figure 2A:
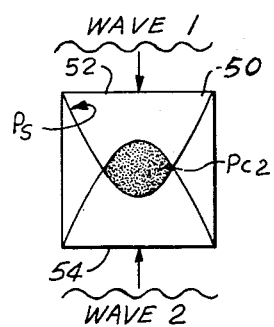
Figure 2B:
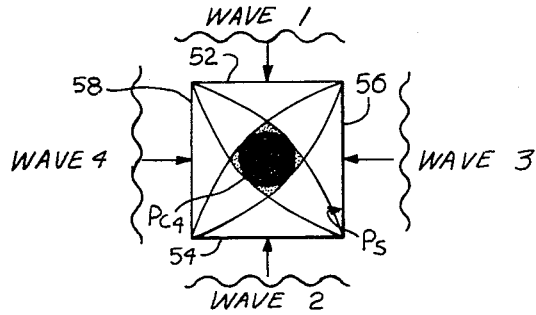

The simplified specimen 50 and radiation wave configuration of FIG. 2b is quite closely approximated, as shown in FIG. 2c, by the cylindrical specimen 20 surrounded by the annular applicator apparatus 12, shown divided into the four 90 degree segments 16 from which four synchronous EMR waves are emitted into the specimen. Hence, central region power densities and specimen heating similar to those discussed above for the square specimen 50 can be expected to occur.

Equation (3), expressing the 16 times central power density, $P_{C4}$, caused by irradiating the specimens 50 or 20 from four independent, 90° directions (FIGS. 2b and 2c), however, represents theoretically maximum central region power densities which can be achieved with an annular applicator, since no other independent radiation directions exist for such applicators around cylindrical body parts.

Somewhat different results for a higher loss "phantom" specimen central region power densities can be obtained using data from the above cited article by Johnson and Guy, and by using equations relating to power losses in lossy medium such as may be found in the "Antenna Engineering Hand Book" by H. Jasik, McGraw Hill, Inc., 1961.

By such analysis, specimen central power density, $P_{C1}$, due to a single EMR wave can be calculated to be about 3.13 percent; the corresponding $P_{C4}$ thus being about 50 percent (compared to the above mentioned 70 percent) of $P_S$. Both analyses however, agree relatively closely with applicant's experimental determination on the homogenous "phantom" specimen, which have yielded values of approximately 61 percent for $P_{C4}$.

Even more rigorous calculations of central power densities $P_{C1}$ and $P_{C4}$ can alternatively be made for specific body regions by considering that most body regions are relatively non-homogeneous, being composed of several layers of different tissue types having different water contents. An example of such detailed analysis may be found in an article written by the applicant, entitled "Annular Applicator to Achieve Deep Heating of Cylindrical or Elliptical Tissue," not yet published.

Such more rigorous analyses indicate, as might be expected, that different body regions have different values of central power densities $P_{C1}$, and hence $P_{C4}$. In a human chest region, for example, such analysis indicates that the combined central region power density, $P_{C4}$, may, theoretically, be greater than the values mentioned above. Regardless, however, of the actual or theoretical values of $P_{C4}$, the important point is that additive wave interference from four synchronous EMR waves impinging upon the specimen from the four independent directions provides greatly enhanced specimen central region power density, thereby substantially enhancing central region EMR heating and greatly improving uniformity of EMR heating of a biological specimen for hyperthermic purposes over that which is possible with less than four independent EMR waves.

It is emphasized, however, that the above described central region power density enhancement, with correspondingly enhanced central power region EMR heating, represent an optimum condition which is not necessarily achieved merely by simultaneously irradiating a specimen from several independent directions. These optimumly enhanced central region effects are achieved only when the applied frequency, f, is selected with proper regard to specimen size and composition. If the applied frequency is not properly selected, much lower central region power densities will result and other higher or lower temperature regions, resulting from additive and substractive wave interference, may occur in the specimen.

Applicant's experimental testing has shown that central region power density and heating are maximized in typical tissue specimens, with minimal hot and cold spotting in other specimen regions, when the wave length of the EMR wave in the particular specimen being irradiated is within the approximate range given by the expression:

$$\tfrac{2}{3}d \leq \lambda_{H/L} \leq 2d, \tag{4}$$

wherein d is the specimen diameter or a typical cross sectional dimension of the specimen and $\lambda_{H/L}$ is the specimen wave length corresponding to the applied frequency, f, in H- or L-type material according to specimen type. If the EMR frequency, f, is selected such that $\lambda_{H/L}$ is greater than about two specimen diameters, difficulty in obtaining an impedance match, with only slight improvement in central region heating has been observed. In contrast, if $\lambda_{H/L}$ is below about two-thirds of the specimen diameter, off-center hot spots have been observed to occur, as have cool spots in other regions. When, however, the applied EMR frequency, f, is selected so that corresponding wavelength is within the range expressed in Equation (4), substantial additive central region heating, with minimal undesirable hot and cold spotting elsewhere, has typically been found to occur.

Procedurally, given (or assuming) a specimen diameter, d, the optimum EMR wave length range is determined by Equation (4). From Table I, which lists $\lambda_H$ and $\lambda_L$ for H- and L-Type material for various corresponding EMR frequencies, a range of optimum EMR frequencies for EMR heating of the specimen can then readily be selected.

As an illustration, for a specimen diameter, d, of approximately 33 centimeters (13 inches) corresponding generally to that of chest or pelvic regions of a typical adult, Equation (4) indicates that a wavelength, $\lambda_{H/L}$ between about 22 and 66 centimeters should be selected for best specimen heating uniformity. Considering that the specimen may include both H- and L-type regions, because of various layers of skin, muscle, fat and bone, Table I indicates that a corresponding EMR frequency, f, of approximately 100 MHz is preferably selected for specimen irradiation, the corresponding wavelengths $\lambda_H$ of 27 cm and $\lambda_L$ of 106 cm being close to the optimum 22–66 cm wave length range.

Table I also shows that a frequency, f, lower than 100 MHz could alternatively have been selected for pure H-Type specimens and a frequency greater than 100 MHz could have been selected for pure L-Type specimens. From Table I it is also seen, for example, that for smaller specimen diameters, a higher frequency, f, is necessary to correspond to the lower optimum $\lambda_{H/L}$ range associated with the smaller diameter. As an illustration, to enable uniform EMR hyperthermia in a limb having a diameter of about 20 centimeters (8 inches), the wave length from Equation (4) should be between about 13 to 40 centimeters, Table I then indicating that an EMR radiation frequency, f, of 100 to about 200 MHz is preferably selected.

From the foregoing discussion, it is apparent that none of the FCC allocated diathermy frequencies of 13.5, 27.12, 40.68, 915, 2450, 5800 and 20,125 MHz are optimum for EMR heating of other than relatively large or small diameter specimen by an annular applicator apparatus, such as the apparatus 12. Use of these FCC allocated diathermy frequencies for more common specimen sizes can therefore be expected to result in undesirably high thermal gradients and/or undesirable hot and cold spotting in the specimens.

Assuming an optimum EMR heating frequency or frequency range is selected for the system 10, in accordance with the above described procedure, there remains the important consideration of providing good impedance matching between the applicator apparatus 12 and the specimen 20 which "loads" the apparatus. Such apparatus 12-to-specimen 20 impedance matching involves, as more particularly described below, determining the size of the apparatus emitting aperture 22 in accordance with size and characteristics of the specimen at the selected EMR frequency, f.

Impedance matching between the apparatus 12 and the specimen 20 is important for several reasons, some of which are well known to those skilled in the microwave art. In the absence of good emitting apparatus-to-load impedance matching, it is well known, for example, that applied EMR energy is reflected back into the emitting system from the load. The resulting effect in the described EMR system 10 would be that to protect the source 32 from the reflected wave energy, ordinarily expensive tuning means (not shown) would be required in the transmission line 34 near the source. In addition, because energy from the resulting standing waves set up in the system 10 must be dissipated in the system as heat, generally more expensive, heat resistant system components than otherwise necessary would be required, further adding to system expense.

In spite of poor apparatus 12-to-specimen 20 impedance matching, the system 10, when provided with the mentioned tuning means and heat resistant components, could normally be overdriven to deliver the amount of EMR power to the specimen required for EMR hyperthermia purposes. However, providing such overdriving capabilities would necessitate that the source 32 have a much higher output power capability than is needed for conditions of good load impedance matching; thereby further substantially adding to cost of the system 10.

Furthermore, poor load impedance matching, by causing standing EMR waves to be set up in the system, generally results in much higher EMR radiation leakage, which may be potentially harmful to system operators and observers, than would otherwise occur. Accordingly poor load impedance matching may result in the requirement for costly system EMR leakage shielding.

An additional important problem particularly associated with EMR hyperthermia apparatus, especially annular applicator apparatus, is that poor specimen impedance matching tends to cause localized regions of EMR energy concentrations in the specimen which cause undesirable hot spotting. In such an annular applicator systems as the system 10, poor impedance matching specimen hot spotting tends to result from the specimen 20, when part of a human body, not being circular in cross section, but having projecting regions which are closer to the emitting aperture 22 than other specimen regions. In regions of lowest specimen-aperture separation, much preferred EMR energy flow paths exist under poor impedance matched conditions, thereby causing high EMR energy density concentrations in the closest spaced specimen regions.

Still further, it has been found that reasonably broad band operation of the system 10 is possible if good specimen load impedance matching is provided for the specimen 20 at the optimum EMR frequency, f. That is, if the load impedance matching at the optimum EMR frequency, f, as determined in the above described manner, is good, the system 10 can ordinarily be operated over a reasonably wide frequency range about the optimum frequency without excessive specimen hot spotting, source power requirements, radiation leakage and so forth.

Such broad band system capability is an important advantage since it enables a given applicator apparatus 12 and system 10 to be effectively used with the variety of specimen sizes and compositions normally expected to be encountered in human beings. Thus, for example, a single apparatus 12 can be effectively used for the normally expected variations in human trunk size and composition, the optimum EMR frequency being selected for each such variation. Accordingly, system costs are minimized since ordinarily only two or three sizes of the applicator apparatus 12 are needed for most specimen sizes and types.

A starting point for impedance matching the apparatus 12 to typical specimens 20 is the characteristic impedance, $Z_o$, of free space. It is universally known that the impedance of free space is approximately 377 ohms per square; that is, a load impedance of 377 ohms is "seen" when radiating into free space through a square emitting aperture. If, however, the emitting aperture, such as the aperture 22, is not square, a different load impedance is seen, the load impedance, $Z_o$, being given by the expression:

$$Z_o = h/w \, 377 \tag{5}$$

in which h and w are the height and width (or length), respectively, of the aperture, and polarization of the emitted wave is parallel to the h dimension. The h/w ratio may be referred to as the aperture aspect ratio.

Figure 3A:
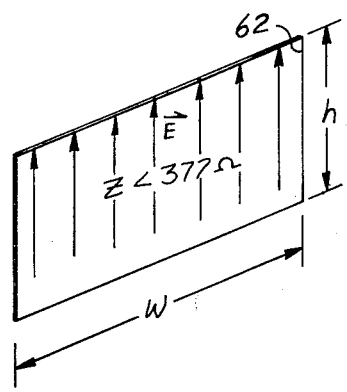
FIG. 3a illustrating the effect of an aperture having a height-to-width ratio greater than one and FIG. 3b illustrating the effect of an aperture having a height-to-width ratio of less than one.
Figure 3B:
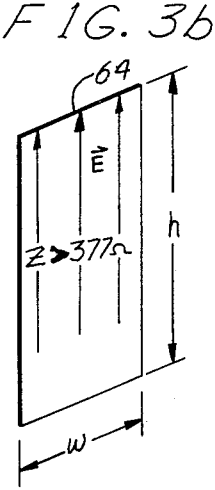
FIG. 3 is a diagramatic representation illustrating the effect of EMR emitting aperture height to width ratio on load impedance.

As an illustration, and as shown in FIG. 3a, a horizontally elongated EMR emitting aperture 62 having a h/w ratio of less than one "sees" a free space load impedance of less than 377 ohms. In contrast, a vertically elongated EMR emitting aperture 64, FIG. 3b, "sees" a free space load impedance of greater than 377 ohms. Thus, increasing aperture width, w, has the effect of adding electrical impedances in parallel while increasing aperture height h, has the effect of adding electrical impedances in series.

When radiating into a medium other than free space, such as into the specimen 20, Equation (5) becomes:

$$Z_m = h/w \frac{377}{\sqrt{e_m}} \text{ ohms,} \tag{6}$$

wherein $Z_m$ is the impedance of the medium and $e_m$ is the dielectric constant of the medium.

For the cylindrical surface aperture 22 which has a diameter, D, Equation (6) becomes:

$$Z_m = \frac{h}{\pi D} \frac{377}{\sqrt{e_m}} \tag{7}$$

It is to be noted that the aperture diameter, D, rather than the specimen diameter, d, is used in Equation (7) since the specimen is "seen" by all regions of the aperture 22. Additionally, by filling the spacing S between the aperture 22 and the specimen 22 by the water filled bolus 26, the entire aperture diameter, D, is filled with specimen-like material, the dielectric constant of distilled water used in the bolus being close to the dielectric constant of human tissue.

From Equations (6) and (7), it is apparent that once the specimen dielectric constant $e_m$ has been determined, there is freedom in varying the aperture aspect ratio to obtain whatever load impedance may be desired. This is particularly advantageous in that freedom to select the load impedance, $Z_m$, of any specimen in this manner enables, as will become more apparent, constructing the applicator apparatus of one or more 50 ohm applicators matching the 50 ohm impedance of typical, commercially available EMR sources, transmission lines, and so forth which may accordingly be used in the system 10 for cost effectiveness.

To determine the appropriate, correct value of dielectric constant, $e_m$, to use in Equations (6) and (7), it is to be appreciated that the dielectric constant of materials exemplified by the specimen 20 depends not only upon the material type but also upon the radiating frequency. That is, a given specimen 20 will present different load impedances to the apparatus 12 at different radiating frequencies, the value of $e_m$ generally decreasing with increasing frequency.

The dielectric constant of lossy materials is also known, in mathematical terms, to comprise a complex value $e_m^*$, given by the equation:

$$\frac{e_m^*}{e_o} = e_{mr} + j\, e_m'' \qquad (8)$$

$e_{mr}$ and $e_m''$ being, respectively the real and imaginary dielectric constant components, and $e_o$ is the permitivity of free space.

TABLE 2

| Applied Frequency f-MHz | Real Dielectric Comp., $e_{mr}$ | | Imag. Dielectric Comp., $e_m''$ | |
|---|---|---|---|---|
| | H-Type | L-Type | H-Type | L-Type |
| 27.12 | 113 | 20 | 406 | 28.5 |
| 40.68 | 97.3 | 14.6 | 306 | 23.3 |
| 100 | 71.7 | 7.45 | 160 | 13.7 |
| 200 | 56.5 | 5.95 | 115 | 8.5 |
| 300 | 54 | 5.7 | 82 | 6.4 |
| 433 | 53 | 5.6 | 59.4 | 4.9 |
| 750 | 52 | 5.6 | 36.9 | 3.3 |
| 915 | 51 | 5.6 | 31.5 | 2.9 |

Listed in Table 2, for the EMR frequencies, f, of Table I, are the corresponding values of the real and imaginary dielectric constant components, $e_{mr}$ and $e_m''$, for both H- and L-type materials. It may, for example, be seen from Table 2 that the real and imaginary dielectric constant components, $e_{mrH}$ and $e_m''{}_H$ for H-type material are substantially higher than the corresponding components $e_{mrL}$ and $e_{mL}''$ for L-type material, and that above 200 MHz, the real components vary little with frequency, f.

Although Equation (8) indicates that the complex dielectric constant, $e_m^*$, should be used to determine load impedance or aspect ratio in Equations (6) or (7), it has been found that for most types of biological materials use of just the real dielectric constant component, $e_{mr}$, in these Equations yields value of $Z_m$ (given a h/w ratio) which agree closely with experimentally determined load impedances.

By way of illustrative example of use of Equation (7) in determining configuration of the apparatus 12, it may be assumed, in furtherance of the above example, that an EMR frequency, f, at 100 MHz has been selected to irradiate a 30 cm diameter, H-type specimen. From Table 2, the corresponding real dielectric constant component is seen to be 71.7. Substituting $e_{mr}$ equal to 71.7 in Equation (7), the expression for the specimen load impedence, $Z_m$, becomes:

$$Z_m = \frac{h}{\pi D} \times \frac{377}{\sqrt{71.7}} \qquad (9a)$$

$$Z_m = h/D \times 14.17 \qquad (9b)$$

Equation (9a) indicates that the characteristic load impedance of the exemplary specimen is 44.5 ohms/-square (for h/w equal to one).

Continuing the example and assuming the particular applicator apparatus 12 to be used is constructed of the four circumferentially arranged segments 16 shown arranged in parallel in FIG. 1, each segment to have 50 ohms impedance, it is seen that the desirable specimen load impedance to the apparatus is 50 ohms divided by 4, or 12.5 ohms. The corresponding emitting aperture 22 height-to-diameter ratio h/D is seen from Equation (9b) to be 0.88. Further assuming an aperture diameter, D, of about 50 cm is desirable for the 30 cm diameter specimen, the corresponding optimum aperture height, h, is determined to be 44 cm for load impedance matching. Each of the four segments 16 would thus preferably be about 44 cm high by about $\pi \times 50/4$ or 39.3 cm wide.

If, as shown in FIG. 1, each of the applicator apparatus segments 16 is additionally divided into a two by two array of four individual 50 ohm applicators 14, each of the individual applicators would preferably be about 22 cm high by 19.7 cm wide.

In a like manner, for any given or selected type of tissue specimen 20 having a diameter (or typical cross-sectional dimension), d, an optimum EMR irradiation frequency, f, is established from Equation (3) and Table I. From the specimen type and established irradiation frequency, f, a corresponding specimen dielectric constant is determined from Table 2. Then, using Equation (7), specimen load impedance, $Z_m$, and emitting aperture height, h, or diameter, D, are determined, depending upon design objectives or limitations, so as to provide impedance matching with the specimen.

Preferably, as described, the emitting aperture aspect ratio, h/w, is selected to enable use of an annular arrangement of one or more 50 ohm impedance applicators.

It is to be appreciated that selection of an appropriate EMR frequency, f, and irradiating aperture configuration in accordance with the above described method represents theoretical and experimental best results for uniform specimen EMR heating in a safe and relatively economical manner which is not necessarily achieved by all types of applicators or applicator arrays. That is, to realize the optimum benefit achieved by selecting the EMR irradiating frequency and aperture configuration in the above described manner, the individual applicators, such as the applicators 14 in the apparatus 12, each are required to provide a substantially uniform EMR electric field across an individual radiating face or aperture 66 thereof (FIG. 1).

Uniform electric field applicators, such as those disclosed in applicant's prior U.S. patent application Ser. No. 002,584 filed on Jan. 11, 1979 may thus be used to advantages in the annular applicator apparatus 12 shown in FIG. 1.

However, it has been found additionally advantageous to integrate the individual applicators 14 into a composite array in which emitted electric field variations, particularly at edge intersections between the individual applicators 14 are minimized.

To this end it might be expected that use of a very large number of very small, sychronously operated, but individual, applicators would be preferable so that edge effects would be less pronounced and more evenly and closely distributed over the specimen 20. From a practical standpoint, not only is great difficulty and cost involved in constructing and synchronously operating a very large number of small applicators, but use of very large numbers of small applicators in an annular array form is generally unnecessary to provide substantially uniform specimen heating.

Use of two identical, axially stacked first and second circumferential rows 68 and 70 of the applicators 14, as shown in FIG. 1 for the exemplary applicator apparatus 12, has, for example, been determined to provide substantially uniform EMR specimen heating in an axial direction for most types of tissue specimens, including large diameter specimens typical of body chest and pelvic regions. However, for whole body radiation, in which the axial height, h, is required to be quite large, additional circumferential rows of applicators may be required. Alternatively, a variation coaxial applicator configuration, as described below, may be preferred for such applications.

Similarly, substantially uniform EMR specimen heating in a circumferential direction around the specimen 20, has been found to result, even for the mentioned large diameter specimens, by arranging eight applicators 14 in circumferential, side-by-side relationship.

Accordingly, the exemplary annular applicator apparatus 12 comprises an annular array of sixteen identical applicators 14 arranged in the two rows 68 and 70 of eight applicators each. For convenience in construction, as well as for other reasons which will become more apparent from the following description, the apparatus 12 is shown divided into the four 90° segments 16, each formed of a two-by-two array of the applicators 14, and each being separately fed electromagnetic energy from the source 32, as described below.

Figure 4:
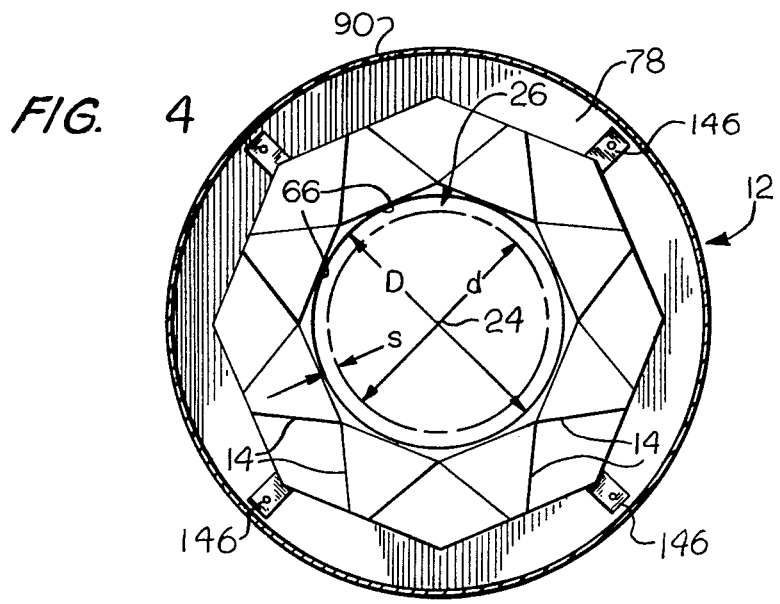
FIG. 4 is a transverse cross-sectional view, taken along line 4-4 of FIG. 1, showing internal configuration of the applicator apparatus of FIG. 1.

The annular applicator apparatus 12 is thus a composite applicator structure formed of the sixteen applicators 14, the emitting aperture 22 being a generally cylindrical, composite aperture defined by sixteen individual applicator radiation emitting apertures 66 (FIG. 4). For the double row of eight applicators 14 each, normal lines from adjacent apertures 66 are at 45° angles, with an angle of 135° between the adjacent apertures.

Figure 5:
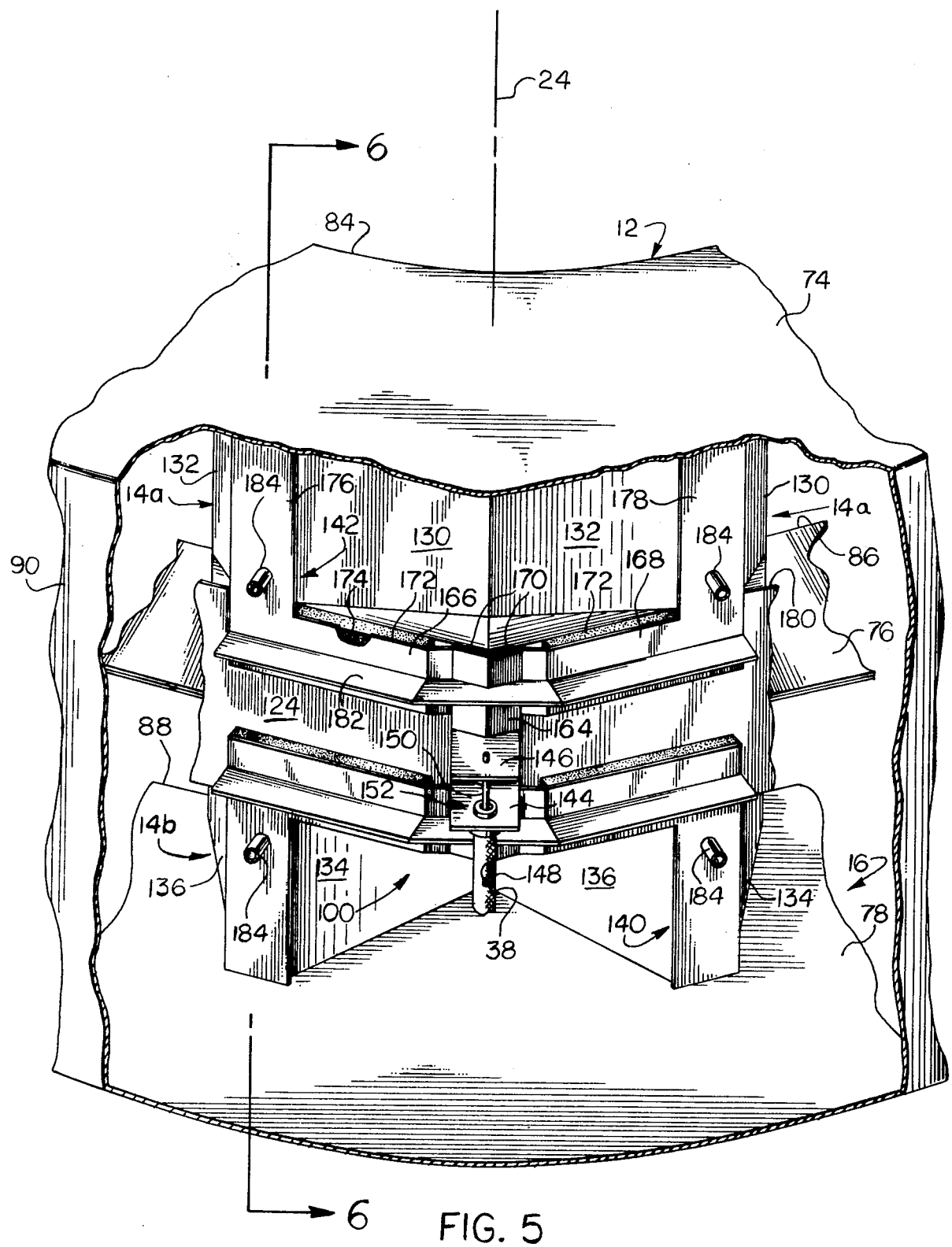
FIG. 5 is a partially cut away perspective drawing of EMR receiving portions of a typical one of the applicator segments of the applicator apparatus of FIGS. 1 and 4, showing parallel plate EMR transmission line portions thereof.

As shown in FIG. 5, the applicator apparatus 12, is integrated into a composite structure by upper, intermediate (or central) and lower conductive, annular plates 74, 76 and 78, respectively, corresponding circular inner peripheral edges 84, 86 and 88 of which define the applicator apparatus opening. The plates 74, 76 and 78, preferably formed of copper, form ground planes. An outer conductive sheet 90 is electrically connected to peripheral outer edges 94 and 98, respectively, of the upper and lower plates 74 and 78 and encloses the apparatus 12 outwardly of a series/parallel EMR energy receiving portion 100 (FIG. 6), as described below. For purposes of better showing such EMR receiving portion 100, the outer sheet 90 is shown largely cut away in FIG. 5.

Figure 6:
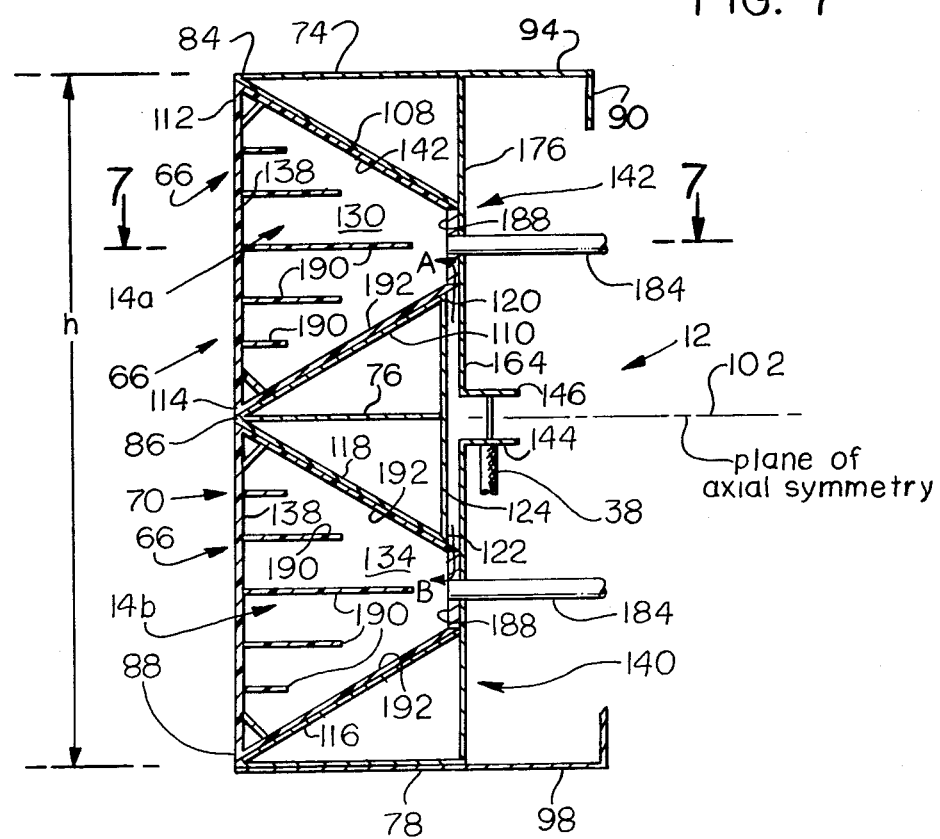
FIG. 6 is a sectional view, taken along line 6-6 of FIG. 5, showing, in elevation, internal configuration of the applicator apparatus of FIG. 1, and features of individual applicators comprising the segment.

Preferably the applicators 14 are constructed, as best seen in FIG. 6, so that the applicator apparatus 12 is axially symmetrical about a central axial plane 102 defined by the intermediate plate 76. A first applicator 14a, typical of the first applicator row 68, comprises radially inwardly and circumferentially diverging first and second conductive plates 108 and 110, respectively, which form an antenna horn-like structure. A radially inner edge 112 of the first plate 108 electrically joins the peripheral inner edge 84 of the upper plate 74. Similarly, a radially inner edge 114 of the second plate 110 electrically joins the inner, peripheral edge 86 of the intermediate plate 76.

Similarly, a second applicator 14b, typical of the second applicator row 70, comprises first and second diverging conductive plates 116 and 118, respectively, radially inner edges of which are electrically joined, respectively, to the edges 88 and 86 of the lower and central plates 78 and 76. Diverging width and spacing between the pairs of plates 108, 110 and 116, 118 are selected to maintain a constant applicator impedance, for example, of 50 ohms.

Radially outer ends 120 and 122, respectively, of all the second plates 110 and 118 are electrically interconnected by an octagonal conductive sheet 124 which is concentric with, but spaced radially inwardly from, the outer sheet 90 and which extends only about one-third the axial height of the apparatus 12.

Figure 7:
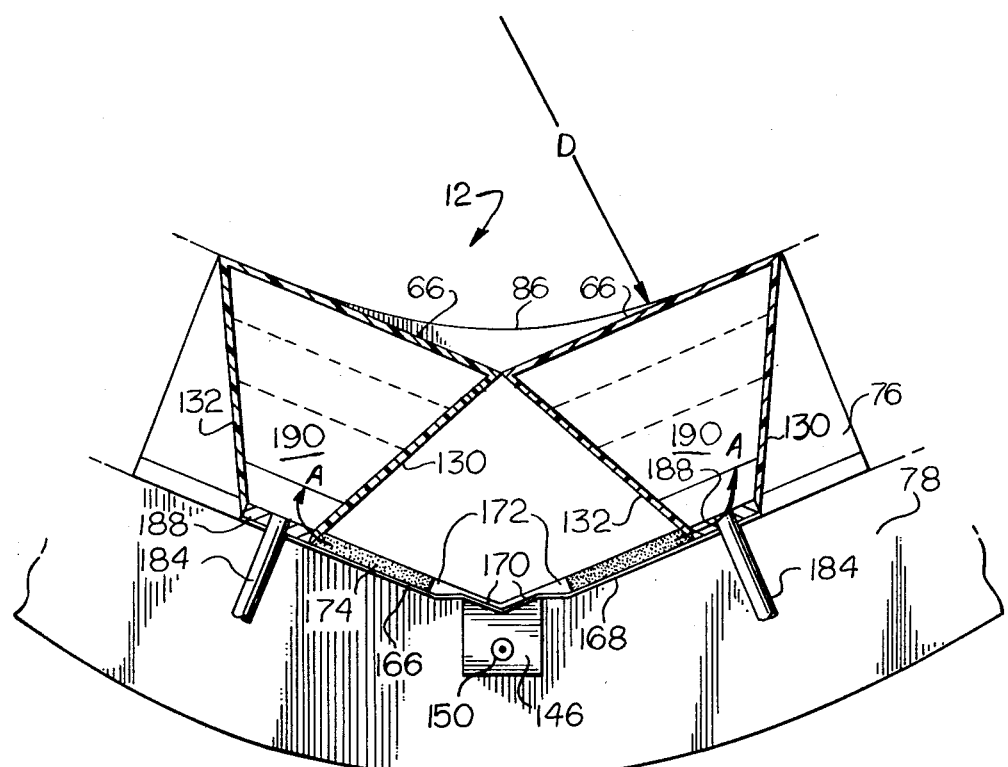
FIG. 7 is a sectional view, taken along line 7-7 of FIG. 6, showing other features of the individual applicators.

Diverging sides of the upper applicator plates 108 and 110 are closed (FIG. 7) by rectangular first and second non-conductive side plates 130 and 132 which are preferably formed from a rigid dielectric material, such as plexiglas. Similar dielectric side plates 134, 136 are used to enclose side regions of the lower applicators 14b. The radiation emitting apertures 66 of all the first and second applicators 14a and 14b are also closed by rectangular dielectric sheets 138 (FIGS. 6 and 7), thereby completely enclosing the applicator.

Electromagnetic energy is supplied to EMR input regions of each of the applicators 14 (14a and 14b) from the second transmission lines 38 through the EMR energy distribution portion 100 of each segment 16. Through the distribution portion 100, which is in parallel plate transmission line form, the second transmission line 38 associated with each of the segments 16 is connected with each of the four associated individual applicators 14.

Each of the four EMR distribution portions 100 (only one of which is shown) is generally "H" shaped and includes first and second conductive strips 140 and 142, respectively. Projecting radially outwardly from central regions of the strips 140 and 142, respectively, are short, spaced apart ears or tabs 144 and 146 to which the transmission line 38 (shown as a conventional coaxial cable) is connected. An outer cable conductor 148 is electrically connected to the first ear 144; an inner cable conductor 150 extends across a gap 152 between the ears 146 and 148, and is electrically connected to the second ear 146. Width of the gap 152, selected for impedance matching with the line 38 in a known manner, is for example, about one cm (0.4 inch), assuming 5 cm (two inch) wide ears 144 and 146 and 50 ohms impedance of the transmission line 38.

Considering for descriptive purposes the second conductive strip 142, which is more clearly shown in FIG. 5, such strip also includes a short portion 164 to which is orthogonally formed the second ear 146. The strip portion 164 which extends parallel to the applicator axis 24 is spaced radially adjacent the inner sheet 124, a distance forming a 25 ohm parallel plate EMR transmission line therewith.

A short axial distance from the ear 146, in circumferential alignment with EMR input regions of the first applicators 14a, the strip 142 branches into left and right (as seen in FIG. 5) portions 166 and 168, respectively, which extend to the applicators 14a, also radially gapped from the sheet 124 to form parallel plate transmission lines therewith. An initial gap 170 between the portions 166 and 168 and the sheet 124 provides a 25 ohm impedence, the spacing then being stepped to form a wider gap 172 providing a 50 ohm matching impedence for the two related applicators 14a. Assuming a 5 cm (two inch) width of the portions 166 and 168, the gaps 170 and 172 are respectively about 0.5 cm (0.19 inch) and 1 cm (0.4 inch). Low-dielectric spacers 174, such as styrofoam strips, may be used to maintain conductor separation in the gaps 172.

At remote ends of the portions 166 and 168 are, respectively, orthogonal portions 176 and 178 extending in an axial direction into electrical contact with the upper plate 74. Beyond EMR distribution portions of the two applicators 14a, the portions 176 and 178 however extend axially beyond an upper edge 180 of the inner sheet 124, the parallel plate transmission line formed between the member 142 and the sheet 124 stopping at such sheet edge. As seen in FIG. 6, an EMR inlet path, indicated by arrow "A" is formed into input regions of the left hand applicator 14 between intersect regions of the strip portions 166 and 176 and the sheet 124. A similar EMR path is formed in the right hand applicator 14a as well in both the applicators 14b (Arrow "B").

A radial stiffening strip 182 is shown attached across the strip portions 166 and 168 to maintain gap spacing with the sheet 124. A similar strip is shown attached to corresponding regions of the first conductive member 140. The first strip 140, which feeds electromagnetic energy to the lower two applicators 146 from the line 38 is constructed as a mirror image of the described strip 142, no additional description of the first strip being therefore provided.

Interference with EMR coupling of the transmission line 38 into the segment EMR distribution portion 100 is avoided by spacing the outer conductive sheet 90 outwardly from ends of the ears 144 and 146, a distance equal to at least about five times the width of the gap 152, for example, at least about 5 cm (2 inches) for the 1 cm gap mentioned.

Figure 8:
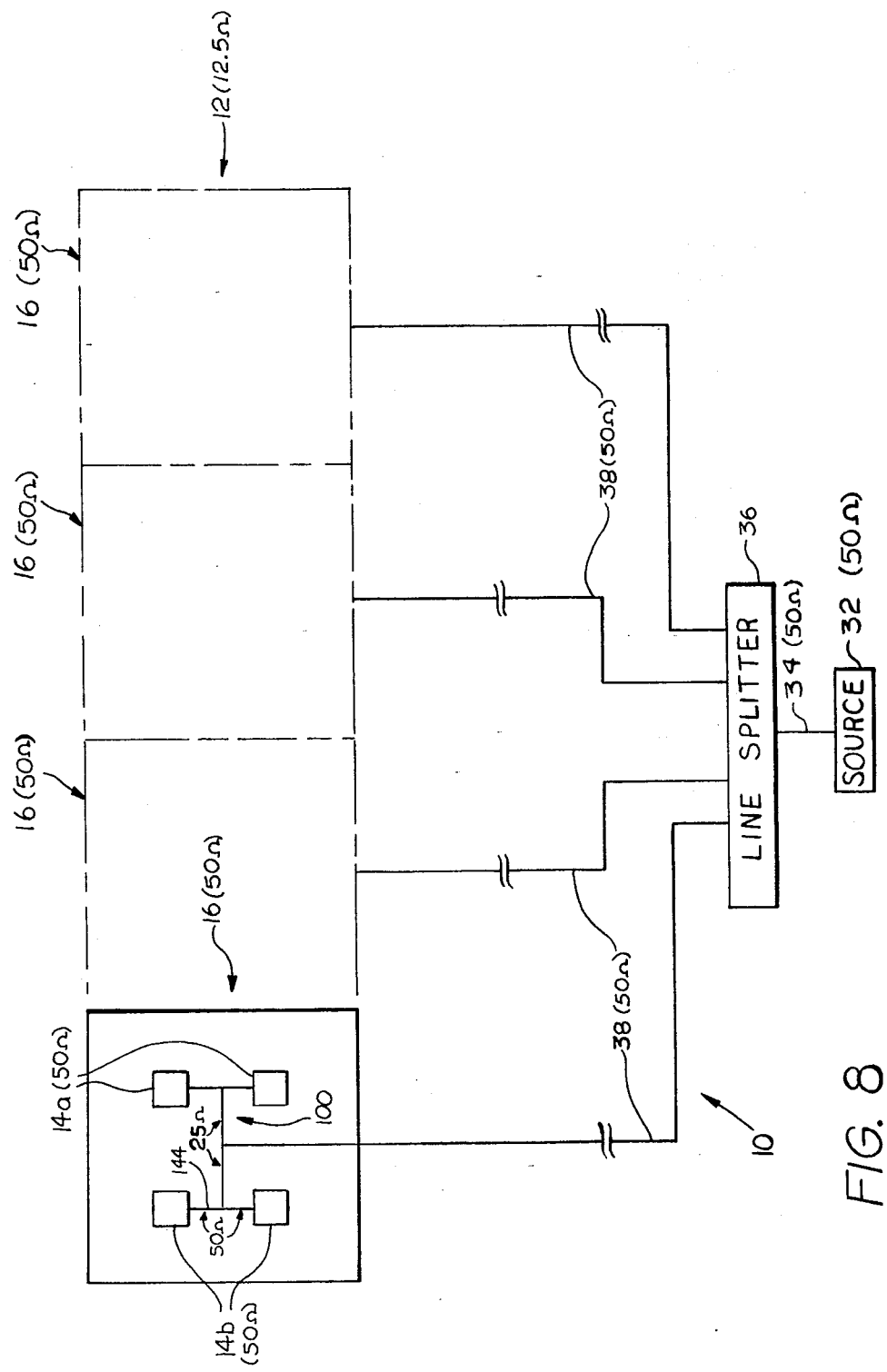
FIG. 8 is a schematic drawing of the EMR system of FIG. 1, showing EMR flow paths and impedances.

With the described configuration of the EMR input portion 100, 50 ohm impedance matching is maintained throughout the entire system 10, from the source 32 to the individual applicators 14 (14a and 14b) which comprise the segments 16 (FIG. 8). Since, however, the four applicator segments 16 are in electrical parallel, the applicator apparatus 12 itself has only a 12.5 ohm impedance. Thus the line splitters 36, which may, for example, comprise standard reactive power dividers available from Microlab/FXR of Livingstone, N.J., also provide impedance matching.

Further, the annular applicator apparatus 12 includes dielectric fluid flow lines 184 through which dielectric fluid, such as distilled water, is supplied to and flowed through the closed applicators 14 (14a and 14b) or at least EMR emitting regions thereof. To enable fluid flow, the lines 184 may be double lines; alternatively, flow openings (not shown) between the applicators 14 may be provided.

By employing a fluid dielectric in the applicators 14, the applicators 50 ohms characteristic impedance can more conveniently be attained than would otherwise be possible. Also, by flowing the dielectric fluid through the applicators 14, by a pump 186 (FIG. 1), cooling of the applicators, and hence of surface regions of the specimen 20, is enabled, thereby enabling improved uniformity of specimen heating, across the entire diameter, d, thereof, as may sometimes be desirable or necessary depending on specimen characteristics. Filling of the applicators 14 with dielectric fluid is further enabled by closing EMR inlet regions of each of the applicators with a dielectric element 188.

To enable convenient and inexpensive use of distilled water as the dielectric fluid, a plurality of thin, axially spaced apart dielectric plates or strips 190 are also disposed within the applicators 14. These strips 190, which extend entirely across the applicators have various lengths and extend from the front aperture sheet 138 progressively shorter distances away from the applicator axes 24 as distance from the axial center of the applicators increases. The strips 190, in conjunction with thin dielectric sheets 192 attached to inner surfaces of the applicator plates 108, 110, 116 and 118, are configured to provide an increasing thickness of solid dielectric towards the applicator axis 24.

In this regard, it has been determined that for the type of construction shown, typical applicators 14 are preferably filled with a material having a dielectric constant of about 38. To enable fluid flow cooling, a liquid dielectric is preferable. Liquids having dielectric constants of about 38 cannot easily be obtained, they are relatively costly. Therefore, it is advantageous to instead use distilled water having a dielectric constant of about 78. This is accomplished by also using the dielectric strips 190 and sheets 192 which avoid using thick wedges of solid dielectric, as would otherwise be necessary. This helps to maintain a uniform energy distribution.

The following expression relates the required dielectric thickness, $t_d$, to a total thickness, $t_t$, at any transverse section of the applicators:

$$\frac{t_d}{t_t} = \frac{\frac{1}{\sqrt{e_r}} - \frac{1}{\sqrt{78}}}{\frac{1}{\sqrt{e_d}} - \frac{1}{\sqrt{78}}} \tag{10}$$

in which $e_r$ is the required dielectric constant (for example, the mentioned 38) and $e_d$ is the dielectric constant of the solid (for example, about 2.2 for the plexiglas used). The 78 represents the dielectric constant of water. Thus, for the dielectric constants mentioned, the ratio $t_d/t_t$ equals about 0.087. This indicates that as height ($t_t$) of the applicators 14 increases towards the axis 24, thickness of the solid dielectric ($t_d$) must increase in order to maintain a constant composite dielectric constant ($e_r$).

Ordinarily the required increase in thickness of the solid dielectric would be accomplished by constructing the dielectric sheets 192 on the applicator plates 108, 110, 116 and 118 in wedge form, such sheets increasing in thickness according to the above relationship, as the axis 24 is approached. However, having a relatively thick dielectric region adjacent edges of the emitting apertures 66 tends to cause undesirable field discontinuities or perturbation across the dielectric.

To approximate forming the solid dielectric in wedge form, while avoiding the field discontinuities associated therewith, the stepped dielectric strips 190 are made of appropriate lengths and are appropriately spaced apart to satisfy the $t_d/t_t$ ratio of 0.087, emitted field discontinuities at each of strips negligibly affecting tissue heating uniformity.

An important advantage associated with the four applicator segments 16 being individually connected to the source 32 is that if non-uniform specimen heating is needed, the EMR tissue heating pattern can be shifted about in the specimen 20, for example, by EMR phase shifting between the segments by operation of one or more of the line stretchers 40 so as to provide a synchronous operation which shifts the energy density pattern in the specimen. Alternatively, by connecting selected ones of the segments 16 to the source 32, for example, by using line splitters which split into only one, two, or three second lines 38 instead of all four lines 38, the specimen heating pattern can be shifted towards the emitting applicator segments or segment.

VARIATION OF FIG. 9

Figure 9:
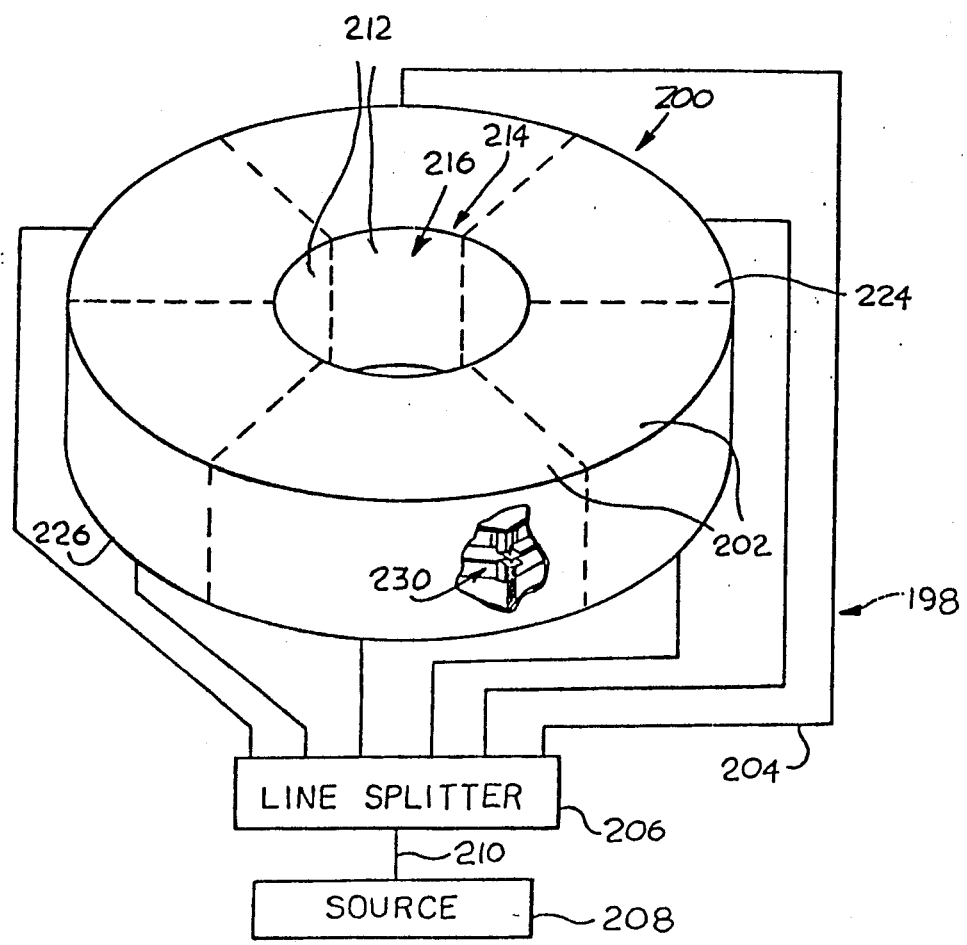
FIG. 9 is a partially cut away and partially schematic perspective drawing, similar to FIG. 1, showing a first variation, hexagonal EMR applicator apparatus and EMR heating system associated therewith.

FIG. 9 illustrates a first variation applicator system 198. In the variation system 198, a hexagonal applicator apparatus 200 comprises an annular, side-by-side arrangement of six applicator segments 202, each of which is independently fed EMR energy by a second transmission line 204 from a line splitter 206. Such splitter 206 is, in turn, connected to an EMR source 208 by a first transmission line 210.

Adjoining EMR emitting apertures 212 of the six applicator segments 202 define a composite, generally cylindrical radiation emitting aperture 214 surrounding an axial, specimen receiving opening 216. Each of the segments 202 comprises a single applicator constructed similarly to the above described individual applicators 14. Thus, the apparatus 200 is formed of a single circumferential row of six single applicators.

Upper and lower, annular conductive ground plates 224 and 226, respectively, of the hexagonal apparatus 200 correspond generally to the upper and lower plates 74 and 76 of the above described applicator apparatus 12. An outer conductive sheet 228 electrically connected to outer peripheral edges of the plates 224 and 226 corresponds to the above described outer sheet 90.

EMR receiving regions of the segments 202 are connected to the coaxial lines 204 by coaxial-to-parallel plate transmission line coupling means 230 similar to the above described coaxial line coupling to the EMR receiving portion 100 of the segments 16, but not requiring the "H" shaped power splitting distribution portion.

If each of the segments 202 comprises a 50 ohm EMR applicator, the combined impedance of the hexagonal applicator apparatus is 50/6 or 8.33 ohms, which is accordingly the load impedance, $Z_m$, of the received specimens which should be seen through (or provided to) the EMR emitting aperture 214.

Assuming, as an illustrative example, the 8.33 ohm apparatus 200 is adapted for irradiating 20 cm (8 inch) diameter specimens, an optimum irradiation frequency wavelength (from Equation (4)) is seen to be between about 13 to 40 cm. Table I indicates a corresponding preferred EMR irradiating frequency, f, of about 100 to 200 MHz. In assumed H-type material, for f equal to 200 MHz, the material dielectric constant, $e_{rh}$, from Table 2, is 56.5. For a diameter, D, of about 25 cm (10 inches) for the emitting aperture 214, a preferred aperture height, h, is calculated from Equation 9a, for a specimen load impedance, $Z_m$, of 8.33 ohms, to be:

$$h = \frac{Z_m \pi D}{377} \sqrt{e_m} , \qquad (11)$$

or about 13.0 cm (5.1 inches).

For uniform EMR heating of generally cylindrical body regions, when axially long heating patterns are unnecessary, the single row, hexagonal applicator apparatus 200 is directly applicable. An advantage of the hexagonal apparatus 200, over the above described four segmented, sixteen applicator apparatus 12, is greater simplicity, and hence lower cost, of construction. Operation of the apparatus 200 is otherwise similar to that described for the applicator apparatus 12, with phase shifting and/or individual operation of the segments 202 preferably being provided. Fluid dielectric filling, with cooling flow provisions, may be provided for the apparatus 200 in the manner described for the apparatus 12, such provisions not being shown, however.

VARIATION OF FIGS. 10 AND 11

Figure 10:
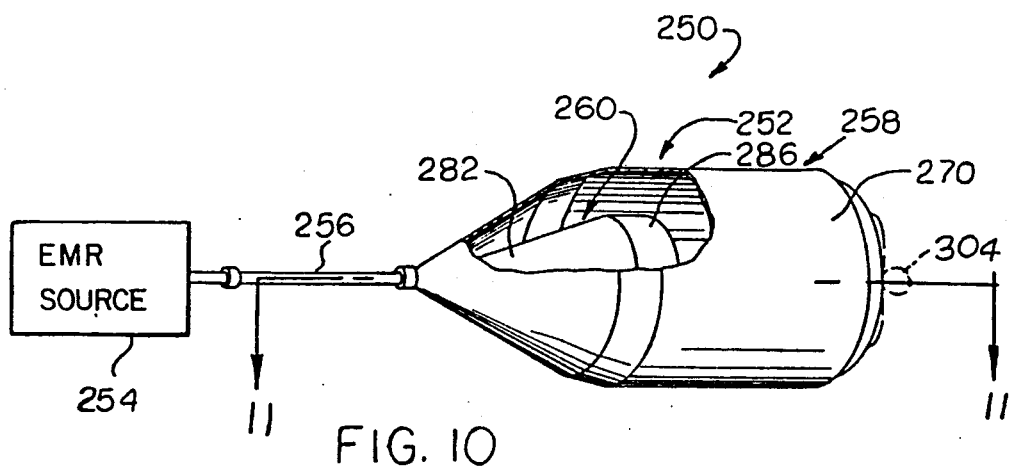
FIG. 10 is a partially cutaway and partially schematic perspective drawing, similar to FIGS. 1 and 2 showing a second variation, coaxial EMR applicator apparatus and EMR heating system associated therewith.
Figure 11:
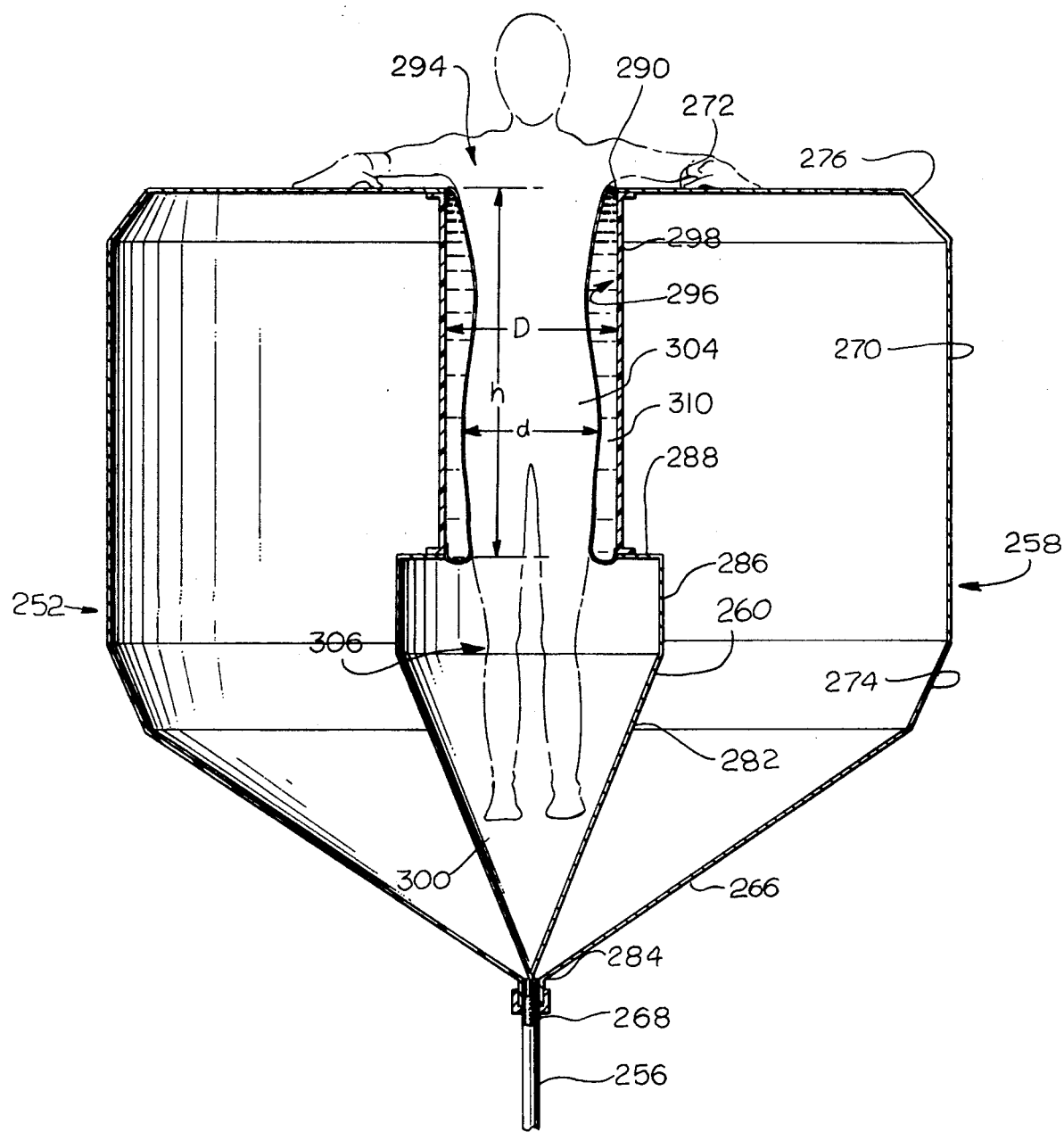
FIG. 11 is a sectional view, taken along line 11-11 of FIG. 10, showing internal configuration of the coaxial applicator apparatus.

FIGS. 10 and 11 illustrate a second variation EMR hyperthermia system 250, according to the present invention, which comprises a coaxial applicator apparatus 252 connected to an EMR source 254 by a single transmission line 256. Preferably the line 256 is a conventional 50 ohm coaxial cable.

Comprising the coaxial applicator apparatus 252 are coaxial outer and inner electrically conductive shells 258 and 260, respectively, both of which are circular in transverse cross section. Spacing between the outer and inner shells 258 and 260 is everywhere maintained to establish a uniform characteristic impedance, for example, 50 ohms, along the apparatus 252. Appropriate shell spacing is determined in accordance with the following expression for characteristic impedance, $Z_o$, of coaxial transmission lines:

$$Z_o = \frac{138}{\sqrt{e}} \log_{10} \frac{d_{(outer)}}{d_{(inner)}} \qquad (12)$$

wherein e is the dielectric constant of material between the outer and inner shells 258 and 260 and $d_{(outer)}$ and $d_{(inner)}$ are respective cross-sectional diameters of the shells. For an air filled coaxial transmission line, such as the apparatus 252, e is equal to one.

Comprising the outer shell 258 is a conical, radially diverging EMR input portion 266, a small diameter, input end of which is electrically connected to an outer conductor 268 of the line 256 (FIG. 11). One end of a generally cylindrical outer shell, intermediate portion 270 is electrically connected to a large diameter end of the conical portion 266. A radially inwardly directed or converging annular terminal end portion 272 is connected to the opposite end of the intermediate portion 270. Inlet and terminal end regions 274 and 276, respectively, of the intermediate portion 270 are preferably made diverging and converging to provide smooth EMR transition between the conical and intermediate portions 266 and 270 and the intermediate and terminal end portions 270 and 272.

Similarly, the inner shell 260 also comprises a conical, radially diverging inlet portion 282, a small diameter end of which is electrically connected to an inner conductor 284 of the transmission line 256. Connected to the large diameter end of the conical portion 282 is one end of a short cylindrical portion 286. A radially inwardly directed or converging annular terminal end portion 288 is connected to an opposite end of the intermediate portion 286.

Inner peripheral edges 290 and 292, respectively, of the two axially spaced apart terminal end portions 272 and 288 define an axial specimen receiving applicator opening 294 of diameter, D. As a result of the outer shell terminal end portion 272 extending axially beyond the inner shell terminal end portion 288, an annular EMR aperture 296, also of diameter, D, and of axial height, h, is defined between the end portions. The aperture 296 and opening 294 are further defined by a tubular, non-conductive member 298 disposed between the terminal end portion inner edges 290 and 292.

Due to the coaxial configuration of the applicator apparatus 252, the specimen receiving opening 294 does not extend entirely through the apparatus. Instead, a generally conical, non-radiating axial chamber 300 is formed within the inner shell 282 in advance of the emitting aperture 296. Thus, for example, as illustrated in FIG. 11, when the coaxial apparatus 252 is sized to irradiate trunk regions of a human body 304, leg regions 306 of the body may extend into chamber 300 and are not irradiated.

Since the apparatus 252 comprises a single applicator, the load impedance of specimens received into the applicator opening 294 preferably equals the apparatus characteristic impedance. By way of illustrative example, assuming an applicator characteristic impedance of 50 ohms, to match with a 50 ohm transmission line 256 and source 254, a 50 ohm specimen load impedance, $Z_m$, is preferred. Further, assuming a whole body size for the apparatus 252, an emitting aperture diameter, D, of about 55 cm (21.65 inches) is selected to receive typical 50 cm diameter, d, body trunk regions. The corresponding preferred emitting frequency, f, is determined to be 100 MHz, in the manner described above for the apparatus 12. (see Table 1)

Substituting into Equation (11), the following expression for the preferred height, h, of the emitting aperture 296 is obtained:

$$h = \frac{50\pi D}{377} \times \sqrt{e_{mr}} \quad (13)$$

If an H-type specimen is assumed, the value for $e_{mr}$ at 100 MHz, from Table 2, is 71.7, which yields a preferred applicator height, h, of about 194 cm (76.4 inches), or just over normal body height.

For either type specimen, good impedance matching between the coaxial applicator apparatus 252 and large diameter tissue specimens requires that the apparatus be axially long, which may be a disadvantage of this type applicator configuration, particularly since a required outer diameter of the apparatus tends to approximate the aperture axial height, h. Furthermore, because of the substantial axial height of the emitting aperture 296, some axial non-uniformity of EMR heating in received specimens may be expected, in spite of axial uniformity of emitted radiation. This may result from composition variations in axially different specimen regions, such as in chest and pelvic regions, and/or from different cross-sectional specimen "fill factors". Although, at least some of the fill factor variations can ordinarily be compensated for by a fluid dielectric, such as distilled water filled bolus 308 installed between the aperture member 298 and specimens like the body 304 so as to eliminate any air gaps.

A significant advantage of the coaxial applicator apparatus 252 is that circumferentially and axially uniform EMR energy distributions are ordinarily achieved around and along the aperture 296, as may be important in cases requiring rapid whole body heating. For example, uniform EMR energy distributions for whole body hypothermic may be important in rapidly elevating a patient's body temperature from hyperthermic conditions associated with some types of medical operations or with low temperature exposure.

Another advantage of the applicator apparatus 250 is relative simplicity of construction, as compared, for example, to the exemplary applicator apparatus 12.

The several above described applicator apparatus 12, 200 and 252, both alone and with their associated EMR, hyperthermia systems 10, 198 and 250, are illustrative of means for implementing the described method for causing substantially uniform and at times centralized EMR heating of biological tissue specimens by selecting an irradiating frequency, f, in accordance with specimen size and type and establishing good specimen-applicator impedence matching by proper emitting aperture configuration. It is again emphasized that providing good impedance matching under specific design conditions enables effective, relatively broad band operation about such conditions, as is frequently desirable to accommodate actual specimen size and type variations normally encountered in use.

Thus, although there have been described above various specific arrangements of annular electromagnetic radiation hyperthermia systems and apparatus, with related methods, in accordance with the invention for purposes of illustrating the manner in which the invention may be used to advantage, it will be appreciated that the invention is not limited thereto. Accordingly, any and all modifications, variations or equivalent arrangements which may occur to those skilled in the art should be considered to be within the scope of the invention as defined in the appended claims.

What is claimed is:

1. An electromagnetic radiation hyperthermia system for causing heating in generally cylindrical biological tissue specimens comprising:
   (a) a source of electromagnetic radiation energy having a preselectable radiation frequency, f;
   (b) an annular applicator apparatus having a specific characteristic impedance and including radiation input portions and means coupled thereto defining a central, axial opening sized to receive the tissue specimens for irradiation thereof; wherein the central opening defining means also defines a peripheral radiation emitting aperture around and along the opening, wherein the aperture comprises a plurality of radiating segments, said aperture having an axial height, h, and circumferential length, w, selected for causing impedance matching at said frequency, f, between the applicator apparatus characteristic impedance and a load impedance of the received specimens as presented to the emitting aperture, and wherein the aperture is configured to cause an enhanced heating region within the specimen; and (c) electromagnetic radiation transmission means for interconnecting said source with the radiation input portions of said applicator apparatus, wherein said transmission means couples energy to each of said radiating segments in a predetermined phase relationship to cause constructive interference in the enhanced heating region.

2. The electromagnetic radiation hyperthermia system as claimed in claim 1, wherein energy generated by said source has a frequency which corresponds to a wavelength in the tissue specimen which is a preselected function of the specimen cross-sectional dimension.

3. The electromagnetic radiation hyperthermia system as claimed in claim 1, wherein the energy generated by said source has a frequency which corresponds to a wavelength in the tissue specimen which is greater than two thirds the specimen cross-sectional dimension.

4. The electromagnetic radiation hyperthermia system of claim 1, wherein said applicator apparatus further includes a flexible, annular, fluid containing envelope disposed around the central opening in a space filling relationship between the applicator apparatus and biological tissue specimens received thereinto, and wherein the fluid has a dielectric constant close to a dielectric constant of the specimen.

5. A method for electromagnetic heating of a generally cylindrical, biological tissue specimen, comprising the steps of:

(a) determining a typical cross-sectional dimension and lossy material properties of typical specimens to be irradiated;

(b) selecting, from said specimen typical cross-sectional dimension and lossy material properties, an electromagnetic radiation heating frequency for causing specimen deep heating;

(c) determining from said selected electromagnetic radiation frequency and specimen lossy material properties, a typical specimen dielectric constant;

(d) encircling the specimen to be radiation heated with an annular applicator apparatus comprised of a plurality of applicator segments, a composite annular radiation emitting aperture of the apparatus being configured to enable, at said selected frequency, impedance matching between the applicator apparatus and a load impedance of the encircled specimen as seen through said composite emitting aperture;

(e) connecting each of said segments individually to a common source of electromagnetic energy;

(f) irradiating the encircled specimen at said selected radiation frequency; and (g) controlling the phase relationship between the radiation emitted by each of said segments to cause a region of constructive interference at a desired location within the specimen.

6. A system for heating tissue specimens or simulations thereof, comprising:

a plurality of radiators coupled together to form an annular array, thereby defining an aperture, wherein said radiators are suitable for emitting transverse electromagnetic radiation radially toward a center of the aperture, and wherein the electric field component of the radiation emitted from each of said applicators is substantially parallel to an axis through the center of the aperture;

source means for causing said radiators to emit transverse electromagnetic radiation having the same frequency; and means for causing the transverse electromagnetic radiation emitted by said radiators to have a predetermined phase relationship, whereby a location is predetermined for a region of constructive interference caused by the radiation emitted by said applicators.

7. The system of claim 6, wherein said source means comprises:

a power source having a selectable frequency output;
a line splitter coupled to said power source for splitting the power source output into a plurality of available outputs having the same frequency and phase;
a plurality of transmission lines coupled to the available outputs and to said radiators for coupling energy to said radiators.

8. The system of claim 6, wherein energy generated by said source means has a frequency which corresponds to a wavelength in the tissue specimen which is a preselected function of the specimen cross-section.

9. The system of claim 6, wherein energy generated by said source means has a frequency which corresponds to a wavelength in the tissue specimen which is greater than approximately two-thirds the specimen cross-section.

10. The system of claim 6, further comprising:
a flexible annular envelope disposed in said aperture adjacent said radiators, wherein said envelope defines a central opening smaller than said aperture; and
dielectric fluid contained within said flexible envelope which presents low resistivity to the passage of transverse electromagnetic radiation therethrough.

11. The system of claim 10, further comprising means for causing said dielectric fluid to flow, thereby cooling surface portions of a specimen located in the central opening.

12. A system according to claim 6 further including a flexible envelope disposed adjacent to said radiators and adapted to be between said radiators and said tissue specimens and dielectric fluid contained within said flexible envelope, said fluid having a dielectric constant close to a dielectric constant of said tissue specimens.

13. The system according to claim 12 further including means for causing said dielectric fluid to flow through said envelope, thereby cooling surface portions of said specimens.

14. A method for deep heating of tissue specimens and simulations thereof, comprising the steps of:

(a) irradiating the specimen from a surrounding, annular radiator having a plurality of radiating portions, wherein the electric field of the radiation is parallel to a central axis of the radiator and the same frequency is emitted by each portion;

(b) controlling the frequency of the radiation;

(c) controlling the power radiated by the individual radiating portions;

(d) determining a desired location for a region of constructive interference between the radiation emitted by the radiating portions; and (e) controlling the phase of radiation emitted by the radiating portions to position the constructive interference region in the desired location.

15. The method of claim 14 further comprising the step of:

(f) changing the size and location of the constructive interference region by varying the controlled radiation properties of steps b, c and e.

* * * * *